US012201391B2

(12) United States Patent
Shuh et al.

(10) Patent No.: US 12,201,391 B2
(45) Date of Patent: Jan. 21, 2025

(54) MEDICAL DEVICES HAVING MULTIPLE BLADES AND METHODS OF USE

(71) Applicant: Intuitive Surgical Operations, Inc., Sunnyvale, CA (US)

(72) Inventors: Christina J. Shuh, Snohomish, WA (US); Ralph Wadensweiler, Sunnyvale, CA (US); Kyle R. Miller, San Jose, CA (US); Jeffrey A. Smith, Petaluma, CA (US); Glenn C. Stante, San Francisco, CA (US); Markus Rheinwald, Kaufering (DE); Hubert Stein, Berlin (DE)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 117 days.

(21) Appl. No.: 17/682,647

(22) Filed: Feb. 28, 2022

(65) Prior Publication Data

US 2022/0183779 A1     Jun. 16, 2022

Related U.S. Application Data

(62) Division of application No. 16/682,591, filed on Nov. 13, 2019, now Pat. No. 11,291,514.

(Continued)

(51) Int. Cl.
*A61B 34/35*     (2016.01)
*A61B 17/00*     (2006.01)
(Continued)

(52) U.S. Cl.
CPC ........ *A61B 34/35* (2016.02); *A61B 17/00234* (2013.01); *A61B 90/37* (2016.02);
(Continued)

(58) Field of Classification Search
CPC ... A61B 34/35; A61B 17/00; A61B 17/00234; A61B 90/37; A61B 19/203; A61B 19/5244; A61B 90/00
See application file for complete search history.

(56) References Cited

U.S. PATENT DOCUMENTS 3,841,317 A     10/1974  Awais
5,052,402 A     10/1991  Bencini et al.
(Continued)

FOREIGN PATENT DOCUMENTS

DE     19537320 A1     4/1997
EP     1151723 A2     11/2001
(Continued)

OTHER PUBLICATIONS

Bean E., et al., "Evaluation of a Novel Atrial Retractor for Exposure of the Mitral Valve in a Porcine Model," The Journal of Thoracic and Cardiovascular Surgery, Dec. 2008, vol. 136 (6), pp. 1492-1495.

(Continued)

*Primary Examiner* — Vi X Nguyen

(57) ABSTRACT

A medical device includes a clevis, a first blade, a second blade, and a tension member. The first and second blades are rotatably coupled to the clevis. The first blade includes a first coupling portion. The tension member is coupled to the first blade and applies a torque to the first blade to rotate the first blade about the clevis between a first, second, and third orientation. The second blade includes a second coupling portion. The second coupling portion is coupled to the first coupling portion such that A) the second blade remains in a fixed position relative to the clevis when the first blade is between the first and second orientation, and B) rotation of the first retractor blade between the second and third orientation transfers at least a portion of the torque to the second (Continued)

retractor blade causing rotation of the second blade about the clevis.

9 Claims, 27 Drawing Sheets

Related U.S. Application Data

(60) Provisional application No. 62/767,661, filed on Nov. 15, 2018.

(51) Int. Cl.
*A61B 90/00* (2016.01)
*A61B 34/00* (2016.01)
*A61B 34/30* (2016.01)

(52) U.S. Cl.
CPC ... *A61B 2034/301* (2016.02); *A61B 2034/305* (2016.02); *A61B 2034/715* (2016.02)

(56) References Cited

U.S. PATENT DOCUMENTS

| | | |
|---|---|---|
| 5,318,589 A | 6/1994 | Lichtman |
| 5,373,854 A | 12/1994 | Kolozsi |
| 5,395,375 A | 3/1995 | Turkel et al. |
| 5,396,900 A | 3/1995 | Slater et al. |
| 5,476,479 A | 12/1995 | Green et al. |
| 5,482,054 A | 1/1996 | Slater et al. |
| 5,490,819 A * | 2/1996 | Nicholas ............ A61B 1/32 |
| | | 606/205 |
| 5,496,317 A | 3/1996 | Goble et al. |
| 5,496,347 A | 3/1996 | Hashiguchi et al. |
| 5,527,339 A | 6/1996 | Koscher et al. |
| 5,575,805 A | 11/1996 | Li |
| 5,582,617 A | 12/1996 | Klieman et al. |
| 5,601,575 A | 2/1997 | Measamer et al. |
| 5,722,935 A | 3/1998 | Christian |
| 5,735,845 A | 4/1998 | Zupkas |
| 5,792,135 A | 8/1998 | Madhani et al. |
| 5,792,165 A | 8/1998 | Klieman et al. |
| 5,855,583 A | 1/1999 | Wang et al. |
| 5,906,630 A | 5/1999 | Anderhub et al. |
| 5,964,780 A | 10/1999 | Balazs |
| 5,968,074 A | 10/1999 | Prestel |
| 6,206,903 B1 | 3/2001 | Ramans |
| 6,214,010 B1 | 4/2001 | Farley et al. |
| 6,273,860 B1 | 8/2001 | Kostylev et al. |
| 6,309,397 B1 | 10/2001 | Julian et al. |
| 6,331,181 B1 | 12/2001 | Tierney et al. |
| 6,368,290 B1 | 4/2002 | Baska |
| 6,394,998 B1 | 5/2002 | Wallace et al. |
| 6,468,265 B1 | 10/2002 | Evans et al. |
| 6,554,844 B2 | 4/2003 | Lee et al. |
| 6,582,451 B1 | 6/2003 | Marucci et al. |
| 6,623,482 B2 | 9/2003 | Pendekanti et al. |
| 6,644,532 B2 * | 11/2003 | Green ............ A61B 17/07207 |
| | | 227/176.1 |
| 6,685,698 B2 | 2/2004 | Morley et al. |
| 6,817,974 B2 | 11/2004 | Cooper et al. |
| 6,840,938 B1 | 1/2005 | Morley et al. |
| 6,843,793 B2 | 1/2005 | Brock et al. |
| 6,949,106 B2 | 9/2005 | Brock et al. |
| 6,964,662 B2 | 11/2005 | Kidooka |
| 6,994,708 B2 | 2/2006 | Manzo |
| 7,083,571 B2 | 8/2006 | Wang et al. |
| 7,090,683 B2 | 8/2006 | Brock et al. |
| 7,125,403 B2 | 10/2006 | Julian et al. |
| 7,147,650 B2 | 12/2006 | Lee |
| 7,169,141 B2 | 1/2007 | Brock et al. |
| 7,214,230 B2 | 5/2007 | Brock et al. |
| 7,338,513 B2 | 3/2008 | Lee et al. |
| 7,371,210 B2 | 5/2008 | Brock et al. |
| 7,445,598 B2 | 11/2008 | Orban et al. |
| 7,608,083 B2 | 10/2009 | Lee et al. |
| 7,824,401 B2 | 11/2010 | Manzo et al. |
| 7,935,130 B2 | 5/2011 | Williams |
| 8,257,371 B2 | 9/2012 | Hamilton et al. |
| 8,479,969 B2 | 7/2013 | Shelton, IV |
| 8,540,748 B2 | 9/2013 | Murphy et al. |
| 8,568,443 B1 | 10/2013 | Jackman et al. |
| 8,758,392 B2 | 6/2014 | Crainich |
| 8,800,838 B2 | 8/2014 | Shelton, IV |
| 9,028,494 B2 | 5/2015 | Shelton, IV et al. |
| 9,078,684 B2 | 7/2015 | Williams |
| 9,204,923 B2 | 12/2015 | Manzo et al. |
| 9,339,341 B2 | 5/2016 | Cooper |
| 9,456,839 B2 | 10/2016 | Cooper |
| 9,554,790 B2 | 1/2017 | Bailey et al. |
| 9,615,846 B2 | 4/2017 | Prestel |
| 9,869,339 B2 | 1/2018 | Zimmerman et al. |
| 9,918,731 B2 | 3/2018 | Cooper et al. |
| 10,130,366 B2 | 11/2018 | Shelton, IV et al. |
| 10,667,873 B2 | 6/2020 | Wallace |
| 10,905,411 B2 | 2/2021 | Racenet et al. |
| 11,259,798 B2 | 3/2022 | Limon et al. |
| 11,291,514 B2 | 4/2022 | Shuh et al. |
| 2004/0087940 A1 | 5/2004 | Jahns et al. |
| 2004/0260198 A1 | 12/2004 | Rothberg et al. |
| 2006/0074415 A1 | 4/2006 | Scott et al. |
| 2006/0184198 A1 | 8/2006 | Bales et al. |
| 2007/0208375 A1 | 9/2007 | Nishizawa et al. |
| 2007/0255109 A1 * | 11/2007 | Stein ............ A61B 34/37 |
| | | 600/214 |
| 2008/0046122 A1 | 2/2008 | Manzo et al. |
| 2008/0065102 A1 | 3/2008 | Cooper |
| 2008/0065105 A1 | 3/2008 | Larkin et al. |
| 2008/0196533 A1 | 8/2008 | Bergamasco et al. |
| 2009/0088774 A1 | 4/2009 | Swarup et al. |
| 2009/0110533 A1 | 4/2009 | Jinno et al. |
| 2009/0131975 A1 | 5/2009 | Ahlberg et al. |
| 2009/0198272 A1 | 8/2009 | Kerver et al. |
| 2009/0209960 A1 | 8/2009 | Chojin |
| 2009/0326530 A1 | 12/2009 | Orban, III et al. |
| 2010/0030238 A1 | 2/2010 | Viola et al. |
| 2011/0295269 A1 | 12/2011 | Swensgard et al. |
| 2011/0295270 A1 | 12/2011 | Giordano et al. |
| 2012/0116433 A1 | 5/2012 | Houser et al. |
| 2013/0144395 A1 | 6/2013 | Stefanchik et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0073856 A1 | 3/2014 | Stein et al. |
| 2014/0100558 A1 | 4/2014 | Schmitz et al. |
| 2014/0243850 A1 | 8/2014 | Sadaka |
| 2014/0276956 A1 | 9/2014 | Crainich et al. |
| 2015/0150584 A1 | 6/2015 | Van Tol |
| 2015/0150635 A1 | 6/2015 | Kilroy et al. |
| 2015/0157355 A1 | 6/2015 | Price et al. |
| 2015/0313676 A1 | 11/2015 | Deodhar |
| 2016/0000423 A1 | 1/2016 | Shields et al. |
| 2016/0287279 A1 | 10/2016 | Bovay et al. |
| 2016/0303743 A1 | 10/2016 | Rockrohr |
| 2017/0333037 A1 | 11/2017 | Wellman et al. |
| 2018/0168572 A1 | 6/2018 | Burbank |
| 2018/0206904 A1 | 7/2018 | Felder et al. |
| 2019/0099227 A1 | 4/2019 | Rockrohr |
| 2019/0192137 A1 | 6/2019 | Shelton, IV et al. |
| 2019/0223960 A1 | 7/2019 | Chaplin et al. |
| 2019/0231374 A1 | 8/2019 | Kimura et al. |
| 2019/0374240 A1 | 12/2019 | Brodbeck et al. |
| 2019/0374297 A1 | 12/2019 | Wallace et al. |
| 2020/0015807 A1 | 1/2020 | Limon et al. |
| 2020/0022765 A1 | 1/2020 | Limon et al. |
| 2020/0054405 A1 | 2/2020 | Schuh et al. |
| 2020/0054408 A1 | 2/2020 | Schuh et al. |
| 2020/0138531 A1 | 5/2020 | Chaplin |
| 2020/0155136 A1 | 5/2020 | Shuh et al. |
| 2020/0155253 A1 | 5/2020 | Shuh et al. |
| 2021/0177534 A1 | 6/2021 | Park |
| 2022/0183711 A1 | 6/2022 | Cooper |

(56) References Cited

U.S. PATENT DOCUMENTS

2023/0189793 A1  6/2023  Ramsey et al.
2023/0190398 A1  6/2023  Limon et al.
2023/0355261 A1  11/2023  Yu

FOREIGN PATENT DOCUMENTS

| WO | WO-2011161626 A2 | 12/2011 |
| WO | WO-2012068156 A2 | 5/2012 |
| WO | WO-2016025132 A1 | 2/2016 |
| WO | WO-2016045041 A1 | 3/2016 |
| WO | WO-2018069679 A1 | 4/2018 |
| WO | WO-2018225196 A1 | 12/2018 |
| WO | WO-2022072732 A1 | 4/2022 |

OTHER PUBLICATIONS

Non-Final Office Action for U.S. Appl. No. 16/682,599 mailed Apr. 27, 2021, 7 pages.

Smith J.M., et al., "Totally Endoscopic Mitral Valve Repair Using a Robotic-controlled Atrial Retractor," The Annals of Thoracic Surgery, Aug. 2007, vol. 84 (2), pp. 633-637.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

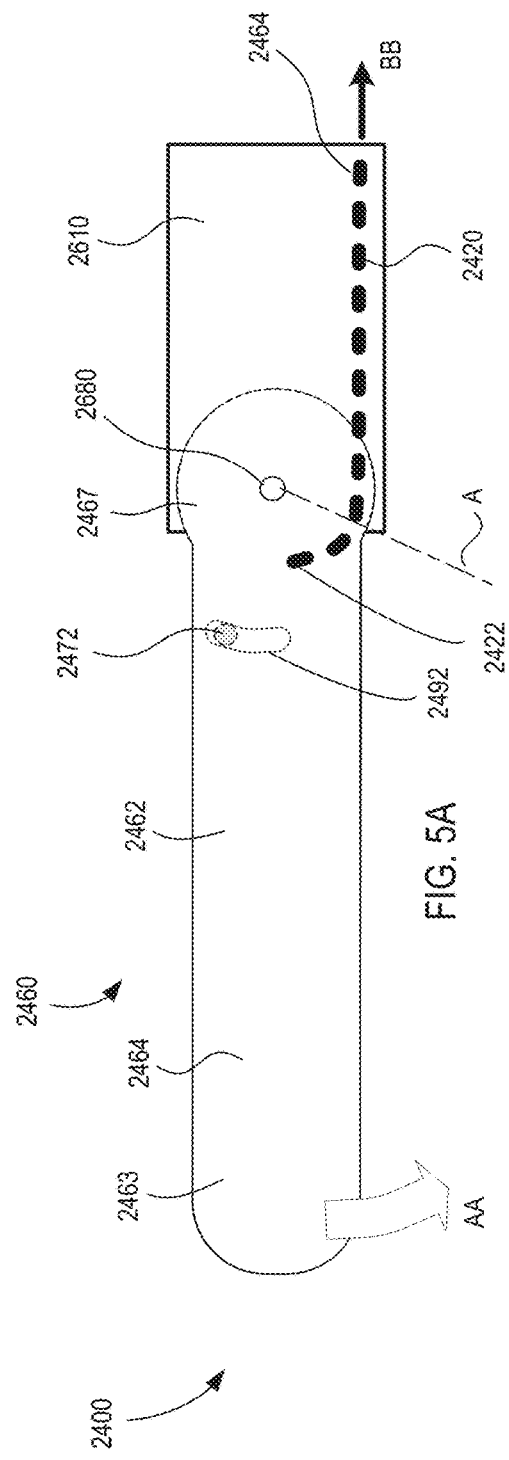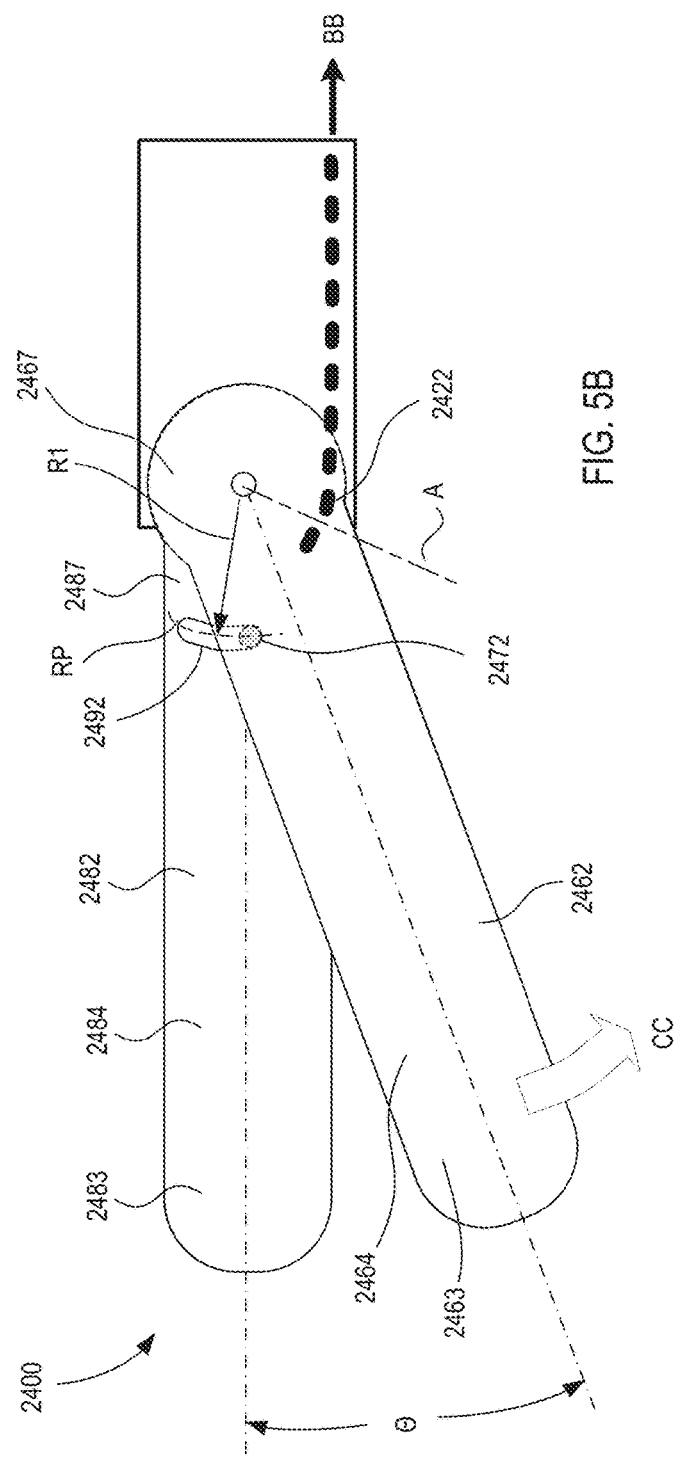
FIG. 5A
FIG. 5B

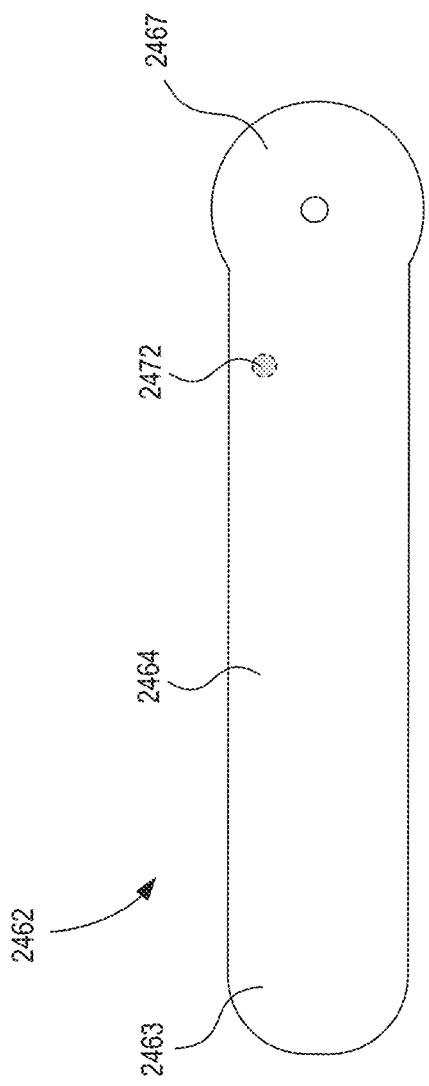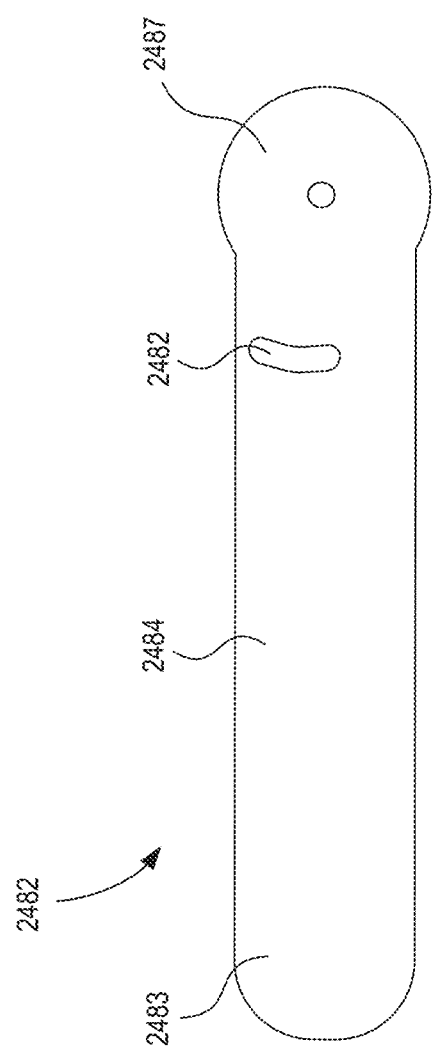

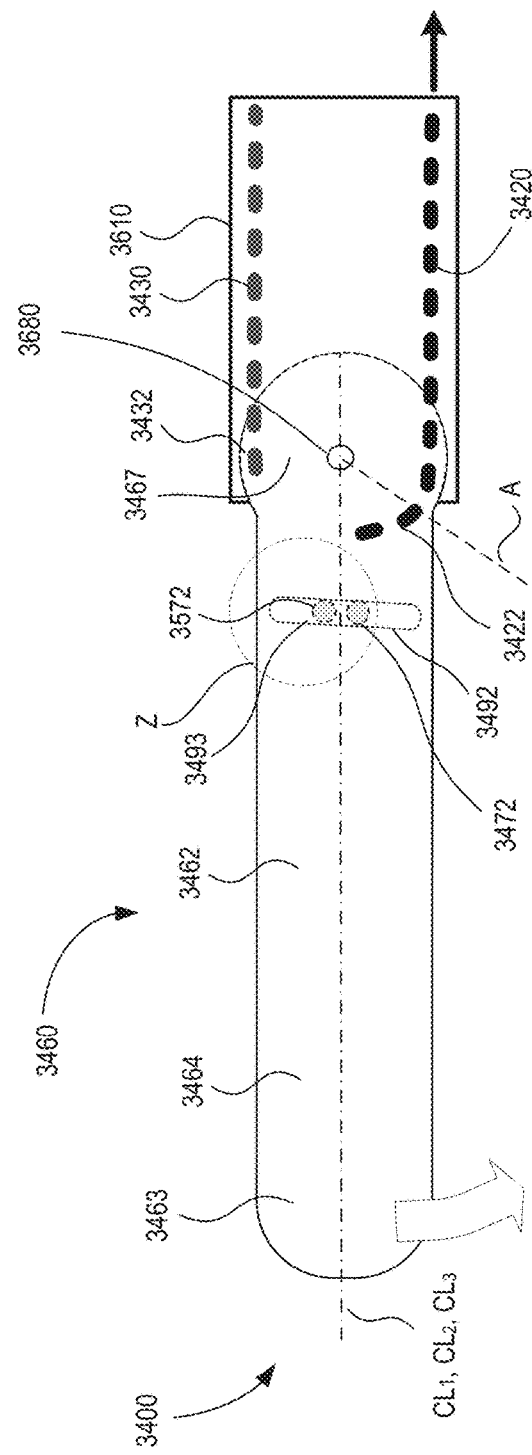
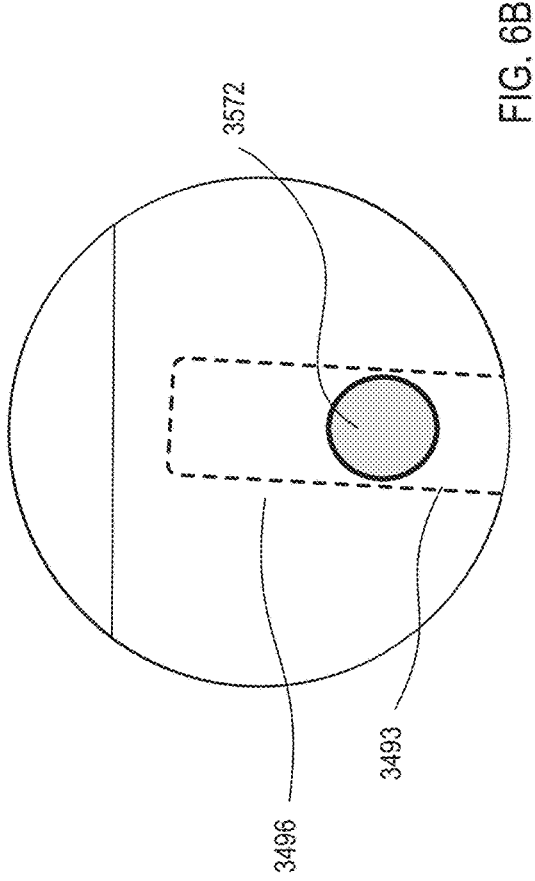
FIG. 6A
FIG. 6B

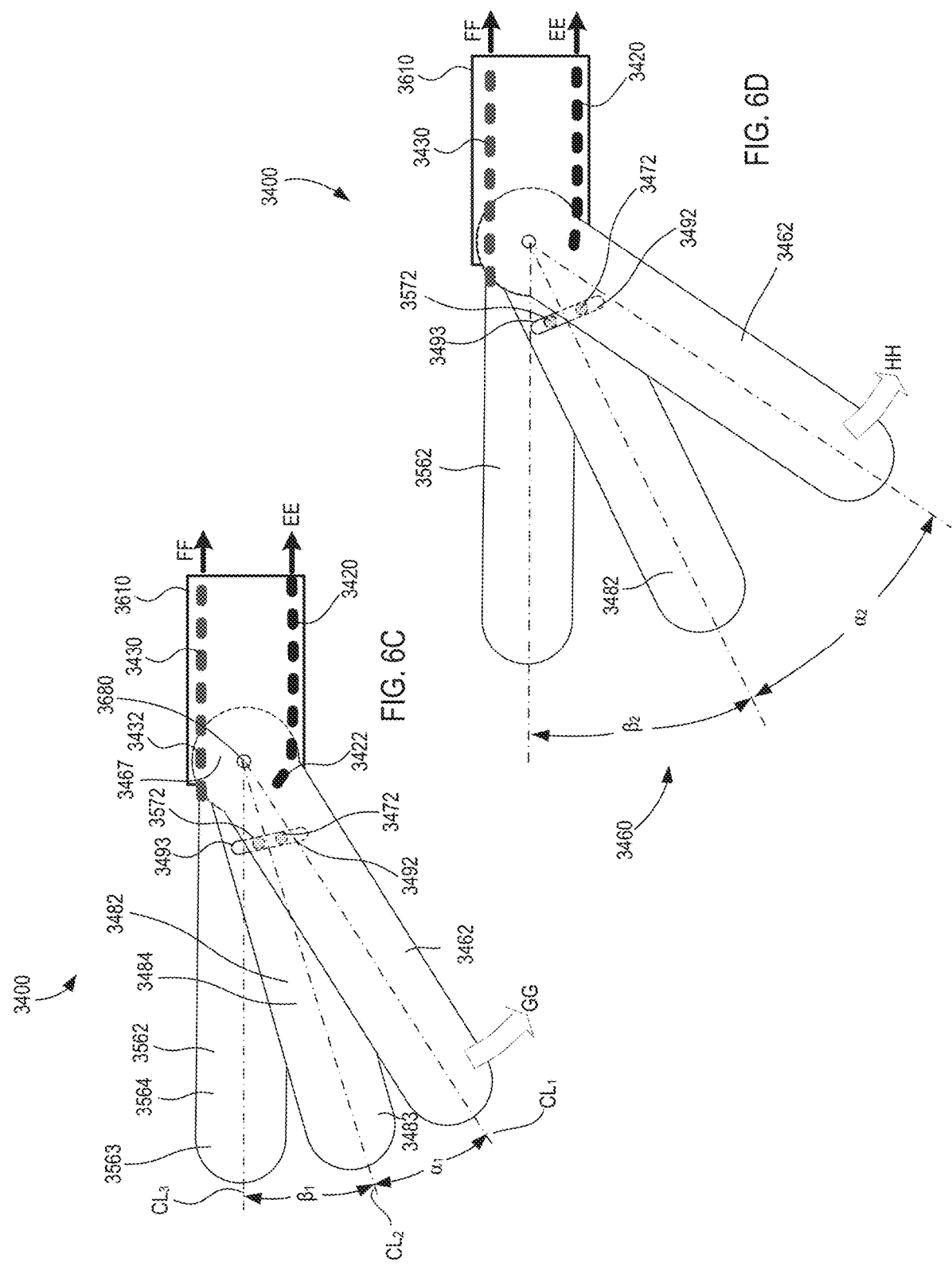

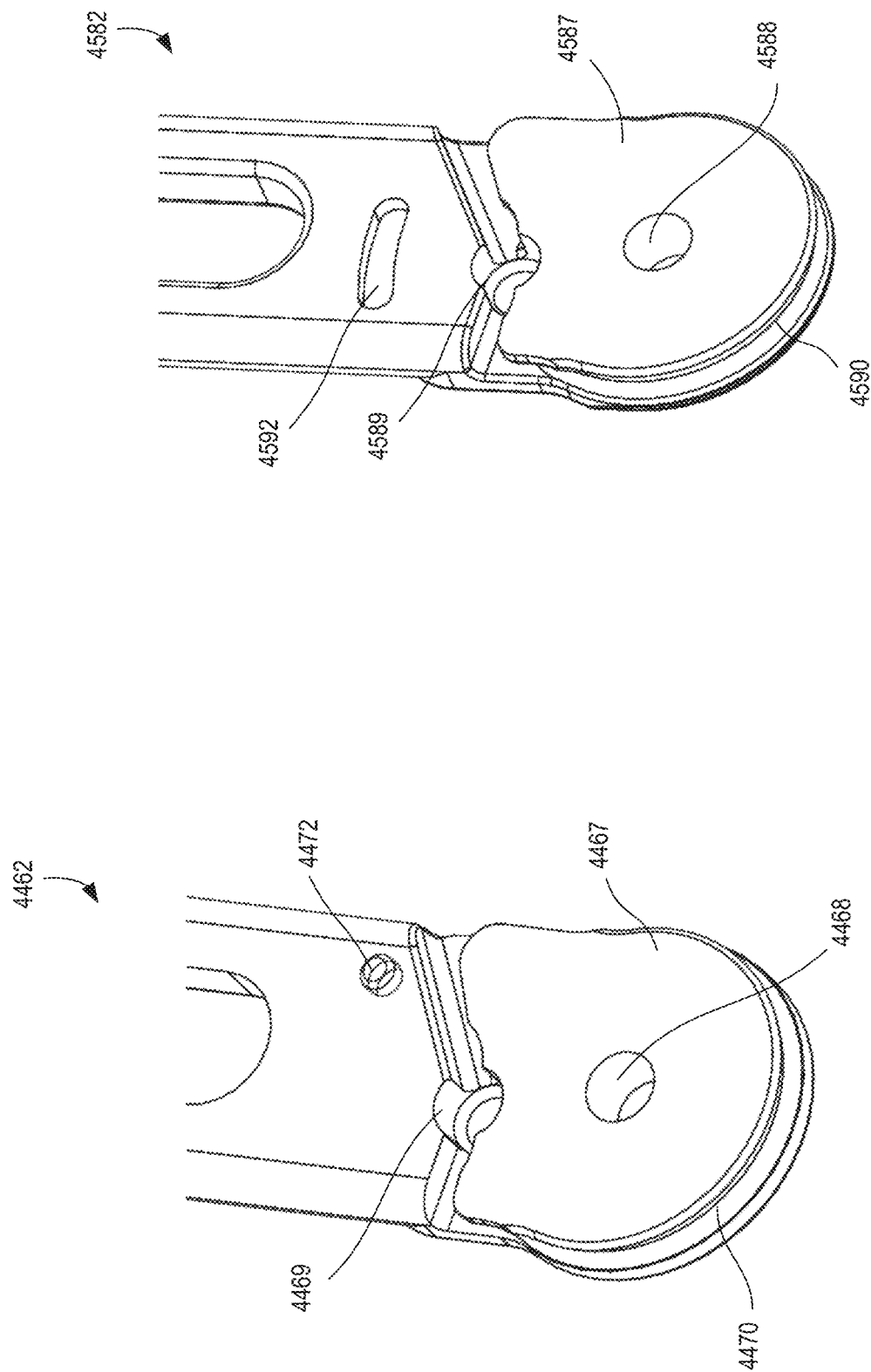

MEDICAL DEVICES HAVING MULTIPLE BLADES AND METHODS OF USE

CROSS-REFERENCE TO RELATED APPLICATION

This application is a divisional of U.S. application Ser. No. 16/682,591 (filed Nov. 13, 2019) (entitled "Medical Devices Having Multiple Blades and Methods of Use"), which claims benefit of priority to U.S. Provisional Application No. 62/767,661 (filed Nov. 15, 2018) (entitled "Medical Devices Having Multiple Blades and Methods of Use"), each of which is incorporated herein by reference in its entirety.

BACKGROUND

The embodiments described herein relate to tissue manipulation tools, more specifically to medical devices, and still more specifically to endoscopic tools. More particularly, the embodiments described herein relate to medical devices having multiple retractor blades that can be used, for example, in surgical applications to hold back tissue, removing tissue, and position (i.e., move) organs during a surgical procedure.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, a tissue retractor, or a cauterizing tool) mounted on a wrist mechanism at the distal end of an extension (also referred to herein as the main tube or shaft). During an MIS procedure, the end effector, wrist mechanism, and the distal end of the main tube can be inserted into a small incision or a natural orifice of a patient to position the end effector at a work site within the patient's body. The optional wrist mechanism can be used to change the end effector's orientation with respect to the main tube to perform the desired procedure at the work site. Known wrist mechanisms generally provide the desired degrees of freedom (DOFs) for movement of the end effector. For example, for forceps or other grasping tools, known wrist mechanisms are often able to change the pitch and yaw of the end effector with reference to the main tube. A wrist may optionally provide a roll DOF for the end effector, or the roll DOF may be implemented by rolling the main tube. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

Known end effectors can include one or more retractor tools to perform retractor functions including engaging tissue or organs to move, hold up, and remove tissue or organs. The retractor tools are designed for engaging tissue or organs in a surgical environment in cooperation with other MIS instruments as part of a clinical procedure. This includes engaging various types of tissues and organs for many different types of procedures. For example, surgical retractors are used to perform preparation functions, such as moving tissue or organs to provide access for other MIS tools, and concomitant functions, such as moving excised tissue away from active surgery functions. Further, surgical retractors are used to perform cooperative functions with other MIS tools, such as dynamically exposing valve structures during mitral valve repair procedure.

Some known surgical retractor tools include multiple retractor blades that are moved by a single drive mechanism to transition the tool between a collapsed configuration for insertion into surgical environment and an expanded configuration for manipulating tissue within the surgical environment. Because the blades are moved via a single drive mechanism (e.g., a gear or pin), this arrangement does not allow for independent movement of the blades of the retractor tool. Such known retractor tools also do not allow the retractor blades to move independently of the other blades. Similarly stated, such arrangements do not allow for some of the blades of the retractor tool to "float" relative to others. Moreover, the single drive mechanism does not allow for independent actuation of blades, which can result in limited rotational range of blades.

Other known surgical retractor tools include two retractor blades that are each actuated by a drive mechanism (e.g., a cable or a rod) that moves the retractor blade. Although this arrangement can provide for independent actuation of each blade, such an arrangement is often not practical where the retractor assembly includes three, four, or more blades.

Thus, a need exists for improved endoscopic retractor tools and methods for tissue manipulation using retractor tools. Improvements may include retractor tools having multiple blades arranged such at least one blade can float relative to other blades. Improvements may also include arrangements in which some blades are driven directly by other blades in a manner that maintains a desired (e.g., centered) spacing between blades.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, an apparatus includes a clevis, a first retractor blade, and a second retractor blade. The clevis defines an axis of rotation. The first retractor blade includes a first coupling portion and a first tissue contact portion and rotates in a first direction about the axis of rotation from a from a first orientation to a second orientation and from the second orientation to a third orientation. The second retractor blade includes a second coupling portion and a second tissue contact portion. The second coupling portion is coupled to the first coupling portion. The first coupling portion and the second coupling portion are configured such that the second retractor blade remains in a fixed position relative to the clevis when the first retractor blade is between the first orientation and the second orientation, and such that rotation of the first retractor blade between the second orientation and the third orientation transfers at least a portion of the torque to the second retractor blade causing rotation of the second retractor blade about the axis. In some embodiments, the second retractor blade is driven solely by rotation of the first retractor blade. In some embodiments, the apparatus includes a tension member coupled to the first retractor blade and that applies a torque to move the first retractor blade. In some embodiments, the tension member is a first tension member and the second retractor blade is devoid of attachment to the first tension member or a second tension member.

In some embodiments, the apparatus further includes a third retractor blade, a fourth retractor blade, and a second coupling feature. The third retractor blade and the fourth retractor blade are each coupled to rotate with the clevis about the axis of rotation. The second coupling feature is between the third retractor blade and the fourth retractor blade. The second coupling feature enables the third retractor blade to rotate without engaging the fourth retractor blade as the third retractor blade rotates in a second direction, opposite the first direction, from the first orientation to a fourth orientation. The second coupling feature enables the third retractor blade to engage and urge the fourth retractor blade to rotate in the second direction as the third retractor blade rotates in the second direction from the fourth orientation to a fifth orientation. In some embodiments, the first retractor blade is mounted outboard of the second retractor blade within the clevis, and the third retractor blade is mounted outboard of the fourth retractor blade within the clevis.

In some embodiments, an apparatus includes a clevis, a first retractor blade, a second retractor blade, and a coupling feature. The clevis defines an axis of rotation. The first retractor blade and the second retractor blade are each coupled within the clevis to rotate about the axis of rotation. The coupling feature is between the first retractor blade and the second retractor blade. The coupling feature enables the first retractor blade to rotate without engaging the second retractor blade as the first retractor blade rotates in a first direction from a first orientation to a second orientation. The coupling feature enables the first retractor blade to engage and urge the second retractor blade to rotate in the first direction as the first retractor blade rotates in the first direction from the second orientation to a third orientation.

In some embodiments, the coupling feature includes a pin received within a slot. In some embodiments, the pin can be located on one of the first retractor blade or the second retractor blade and the slot can be defined by the other of the first retractor blade or the second retractor blade. In some embodiments, the slot can be curved.

In some embodiments, an apparatus includes a clevis, a first retractor blade, a second retractor blade, a third retractor blade, a first coupling feature, and a second coupling feature. The clevis defines an axis of rotation. The first retractor blade, the second retractor blade, and the third retractor blade are each coupled within the clevis to rotate about the axis of rotation. The first coupling feature is between the first retractor blade and the second retractor blade and incudes a first pin received within a first straight slot. The second coupling feature is between the second retractor blade and the third retractor blade and incudes a second pin received within a second straight slot. In some embodiments, the straight slot of the first coupling feature is defined in the third retractor blade, and the straight slot of the second coupling feature is defined in the third retractor blade. In some embodiments the apparatus further includes a clevis pin extending between ears of the clevis. An elongated opening is defined in the third retractor blade with the clevis pin extending through the elongated opening. In some embodiments, the apparatus further includes a first tension member and a second tension member. The first tension member is coupled to urge the first retractor blade to rotate in a first direction about the axis of rotation. The second tension member is coupled to urge the second retractor blade to rotate in a second direction, opposite the first direction, about the axis of rotation.

In some embodiments, an apparatus includes a clevis, a first retractor blade, a second retractor blade, and a tension member. Each of the first retractor blade and the second retractor blade is rotatably coupled to the clevis about an axis. The first retractor blade includes a first coupling portion and a first tissue contact portion. The tension member is coupled to the first retractor blade and is configured to apply a torque to the first retractor blade to rotate the first retractor blade about the axis between a first orientation, a second orientation, and a third orientation. The second retractor blade includes a second coupling portion and a second tissue contact portion. The second coupling portion is coupled to the first coupling portion. The first coupling portion and the second coupling portion are configured such that A) the second retractor blade remains in a fixed position relative to the clevis when the first retractor blade is between the first orientation and the second orientation, and B) rotation of the first retractor blade between the second orientation and the third orientation transfers at least a portion of the torque to the second retractor blade causing rotation of the second retractor blade about the axis. In some embodiments, the second retractor blade is driven solely by rotation of the first retractor blade. In some embodiments, the second retractor blade is devoid of attachment to the tension member or any other tension member.

In some embodiments, the second retractor blade is configured to rotate about the axis independently from rotation of the first retractor blade when the first retractor blade is between the first orientation and the second orientation. Similarly stated, in some embodiments, the second retractor blade is configured to float relative to the first retractor blade when the first retractor blade is between the first orientation and the second orientation. In some embodiments, the axis is a first axis and the clevis is a distal clevis of a wrist assembly. The wrist assembly includes a proximal link coupled to the distal clevis. The distal clevis configured to rotate about the proximal link about a second axis (referred to as a pitch axis) that is nonparallel to the first axis.

In some embodiments, the first coupling portion includes a drive pin extending from the first retractor blade and the second coupling portion includes a slot defined by the second retractor blade. The drive pin is rotatable along a rotation path about the axis when the first retractor blade rotates about the axis. A portion of the drive pin is within the slot, which includes a curved portion aligned with the rotation path. The portion of the drive pin is configured to move within the curved portion slot when the first retractor blade is between the first orientation and the second orientation. The portion of the drive pin is configured to engage a wall defining the slot to transfer the portion of the torque to the second retractor blade when the first retractor blade rotates between the second orientation and the third orientation. In other embodiments, the drive pin can extend from the second retractor blade and the slot can be defined by the first retractor blade.

In some embodiments, the second coupling portion includes a driven pin extending from the second retractor blade. The driven pin is rotatable along a rotation path about the axis when the second retractor blade rotates about the axis. The first coupling portion includes a slot defined by the first retractor blade. A portion of the driven pin is within the slot, which includes a curved portion aligned with the rotation path. The portion of the driven pin is configured to move within the curved portion of the slot when the fist retractor blade is between the first orientation and the second orientation. The portion of the driven pin is within the slot and the slot includes a curved portion aligned with the rotation path. The portion of the driven pin is movable within the curved portion of the slot when the first retractor blade is between the first orientation and the second orientation. A wall defines the slot for engaging the driven pin to transfer the portion of the torque to the second retractor blade when the first retractor blade rotations between the second orientation and the third orientation.

In some embodiments, the apparatus includes a third retractor blade and a second tension member. The third retractor blade is rotatably coupled to the clevis and has a third coupling portion and a third tissue contact portion. The second retractor blade is between the first retractor blade and the third retractor blade and includes a fourth coupling portion. The third coupling portion of the third retractor blade is coupled to the fourth coupling portion of the second retractor blade. The second tension member is coupled to the third retractor blade and configured to apply a second torque to the third retractor blade to rotate the third retractor blade about the axis. In some embodiments, the third retractor blade is directly coupled to the second retractor blade. For example, the third coupling portion can include a drive pin and the fourth coupling portion can include a slot defined by the second retractor blade. A portion of the drive pin can be within the slot such that the drive pin can move within the curved portion of the slot when the third retractor blade is within a first angular range. The portion of the drive pin is configured to engage a wall defining the slot to transfer the portion of the second torque to the second retractor blade when the third retractor blade is within a second angular range.

In other embodiments, the third coupling portion is indirectly coupled to the fourth coupling portion (i.e., via a fourth retractor blade or other intervening structure). In some embodiments, the apparatus includes a fourth retractor blade rotatably coupled to the clevis. The fourth retractor blade has a fifth coupling portion, a sixth coupling portion, and a fourth tissue contact portion. The fourth retractor blade is between the second retractor blade and the third retractor blade. The third coupling portion is directly coupled to the fifth coupling portion of the fourth retractor blade, the sixth coupling portion coupled to the fourth coupling portion of the second retractor blade.

In some embodiments, an apparatus includes a clevis, a first retractor blade, a second retractor blade, a third retractor blade, a first tension member, and a second tension member. Each of the first retractor blade, the second retractor blade, and the third retractor blade is rotatably coupled to the clevis about an axis. The first retractor blade includes a first coupling portion and a first tissue contact portion. The second retractor blade is between the first retractor blade and the third retractor blade and includes a second coupling portion, a fourth coupling portion, and a second tissue contact portion. The second coupling portion is coupled to the first coupling portion. The third retractor blade includes a third coupling portion and a third tissue contact portion. The third coupling portion is coupled to the fourth coupling portion of the second retractor blade. The first tension member is coupled to the first retractor blade and is configured to apply a first torque to the first retractor blade to rotate the first retractor blade about an axis of the clevis to a first angular orientation. The second tension member is coupled to the third retractor blade and is configured to apply a second torque to the third retractor blade to rotate the third retractor blade about the axis of the clevis to a third angular orientation different than the first angular orientation. The first coupling portion, the second coupling portion, the third coupling portion, and the fourth coupling portion are collectively configured such that when the first retractor blade is in the first angular orientation and the third retractor blade is in the third angular orientation, the second retractor blade is in a second angular orientation that is centered between the first angular orientation and the third angular orientation.

In some embodiments, the second retractor blade is configured to be rotated about the axis of the clevis to the second angular orientation by at least one of A) a portion of the first torque transferred to the second retractor blade by the interface of the first coupling portion and the second coupling portion or B) a portion of the second torque transferred to the second retractor blade by the interface of the third coupling portion and the fourth coupling portion.

In some embodiments, the first coupling portion includes a first drive pin extending from the first retractor blade and the third coupling portion includes a second drive pin extending from the third retractor blade. The first drive pin is rotatable along a first rotation path about the axis when the first retractor blade rotates about the axis and the second drive pin is rotatable along a second rotation path about the axis when the third retractor blade rotates about the axis. The second coupling portion includes a first slot defined by the second retractor blade and the fourth coupling portion includes a second slot defined by the second retractor blade. A portion of the first drive pin is within the first slot and a portion of the second drive pin is within the second slot. The first slot has at least one of a first shape or a first orientation corresponding to the first rotation path such that portion of the first torque is transferred to the second retractor blade throughout the first rotation path. The second slot has at least one of a second shape or a second orientation corresponding to the second rotation path such that portion of the second torque is transferred to the second retractor blade throughout the second rotation path. In some embodiments, the first slot and the second slot are configured such that the portion of the first torque transferred to the second retractor blade is within ten percent of the portion of the second torque transferred to the second retractor blade. In some embodiments, the first slot and the second slot are configured such that the portion of the first torque transferred to the second retractor blade is substantially equal to the portion of the second torque transferred to the second retractor blade.

In some embodiments, each of the first slot and the second slot are linear. In some embodiments, a center line of the first slot defines a first slot angle relative to a longitudinal axis of the second retraction blade and a center line of the second slot defines a second slot angle relative to a longitudinal axis of the second retraction blade. The second slot angle is of an opposite sign of the first slot angle. In some embodiments, the first slot is defined within a first side of the second retraction blade and does not extend through the entire second retraction blade. The second slot is defined within a second side of the second retraction blade and does not extend through the entire second retraction blade.

Methods of operating a retractor assembly are also described herein. In some embodiments, a method includes exerting a first torque on a first retractor blade of a retractor assembly to rotate the first retractor blade about a clevis to a first angular orientation. The retractor assembly including the first retractor blade, a second retractor blade, and a third retractor blade. The first retractor blade has a first coupling portion and a first tissue contact portion. The second retractor blade is between the first retractor blade and the third retractor blade and has a second coupling portion, a fourth coupling portion, and a second tissue contact portion. The second coupling portion is coupled to the first coupling portion. The third retractor blade has a third coupling portion and a third tissue contact portion. The third coupling portion is coupled to the fourth coupling portion of the second retractor blade. A second torque is exerted on the third retractor blade to rotate the third retractor blade about the clevis to a third angular orientation. The second retractor blade is rotated relative to the clevis to a second angular orientation between the first angular orientation and the third angular orientation by at least one of A) a portion of the first torque transferred to the second retractor blade by the interface of the first coupling portion and the second coupling portion or B) a portion of the second torque transferred to the second retractor blade by the interface of the third coupling portion and the fourth coupling portion.

In some embodiments, exerting the first torque and exerting the second torque are performed at the same time. In some embodiments, exerting the first torque is performed by moving a first tension member coupled to the first retractor blade and exerting the second torque is performed by moving a second tension member coupled to the third retractor blade.

In some embodiments, the first torque causes the first retractor blade to rotate in a first direction and the second torque causes the second retractor blade to rotate in a second direction opposite the first direction. The method further includes exerting a third torque on the first retractor blade to rotate the first retractor blade about the clevis in the second direction and exerting a fourth torque on the third retractor blade to rotate the third retractor blade about the clevis in the first direction. The retractor assembly is moved from an expanded configuration to a collapsed configuration after the exerting the third torque and the exerting the fourth torque. In some embodiments, the method further includes introducing, when the retractor assembly is in the collapsed configuration, a distal end portion of an elongate instrument into a body cavity, the distal end portion of the elongate instrument including a wrist assembly and the retractor assembly. The wrist assembly includes a proximal link coupled to the clevis such that the clevis is configured to rotate about the proximal link about a second axis (referred to as a pitch axis). The method includes manipulating, after the exerting the first torque and the second torque, a target tissue within the body cavity with any of the first tissue contact portion, the second tissue contact portion, or the third tissue contact portion. The distal end portion of the elongate instrument is then removed from the body cavity after the manipulating and after the exerting the third torque and the fourth torque.

Other medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

BRIEF DESCRIPTION OF THE DRAWINGS

FIGS. 5A-5C are diagrammatic views of a portion of an instrument of a surgery system according to an embodiment with a first blade in a first orientation (FIG. 5A), a second orientation (FIG. 5B), and a third orientation (FIG. 5C).

FIG. 5D is a diagrammatic view of the first blade shown in FIGS. 5A-5C.

FIG. 5E is a diagrammatic view of a second blade of the instrument shown in FIGS. 5A-5C.

FIGS. 6A, 6C, and 6D are diagrammatic views of a portion of an instrument of a surgery system according to an embodiment in a first configuration (FIG. 6A), a second configuration (FIG. 6C), and a third configuration (FIG. 6D).

FIG. 6B is an enlarged view of a portion of the instrument identified as region Z in FIG. 6A.

FIG. 13 is a perspective view of a proximal end portion of a first retractor blade of the instrument shown in FIGS. 8 and 9.

FIG. 14 is a perspective view of a proximal end portion of a third retractor blade of the instrument shown in FIGS. 8 and 9.

DETAILED DESCRIPTION

Figure 1:
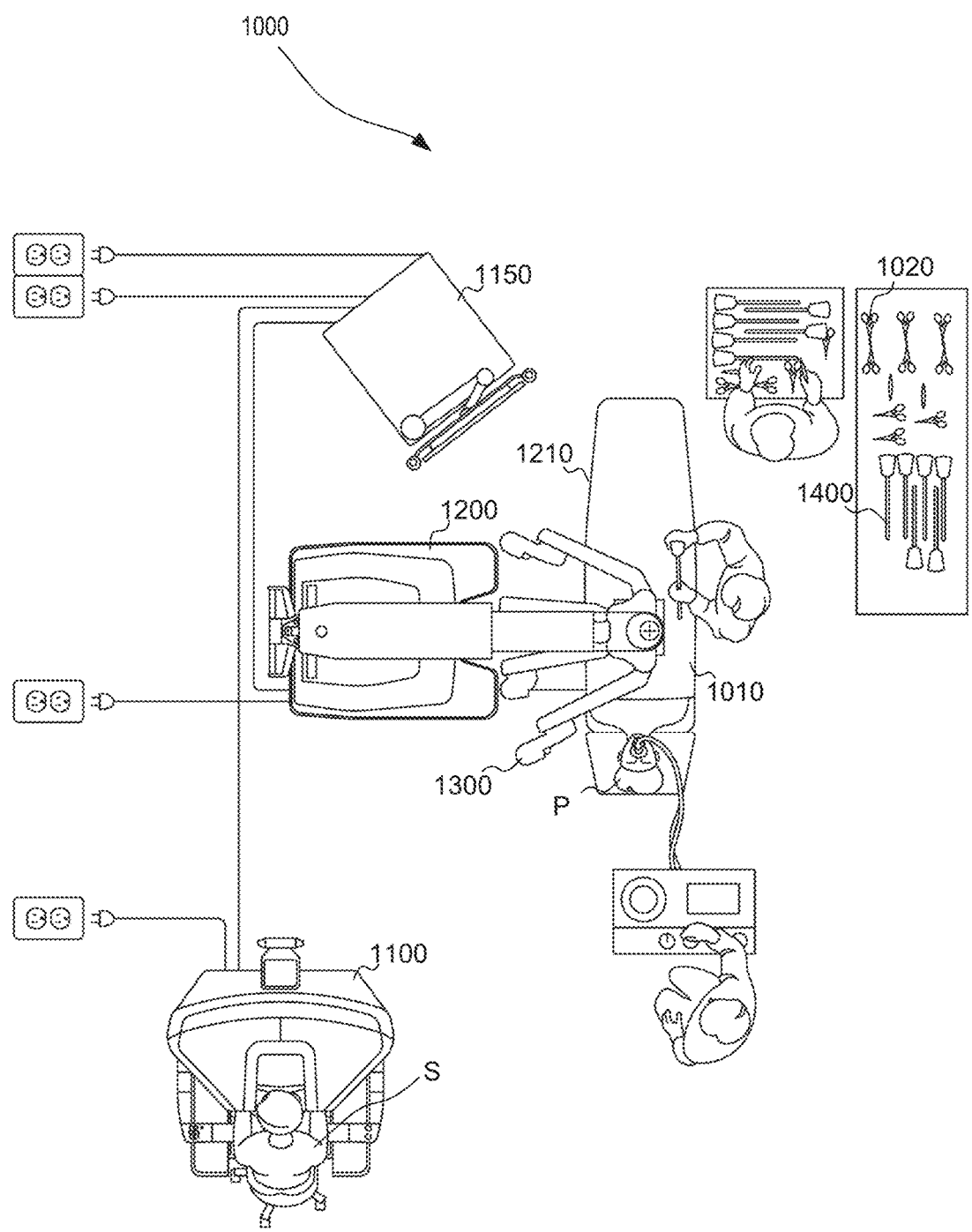
FIG. 1 is a plan view of a minimally invasive teleoperated medical system according to an embodiment, being used to perform a medical procedure such as surgery.

The embodiments described herein can advantageously be used in a wide variety of grasping and manipulating operations associated with minimally invasive surgery. In particular, the instruments described herein can be low-cost, disposable instruments that facilitate being used for only one procedure. Furthermore, instruments described herein can be MIS instruments configured to perform a variety of tissue manipulation operations with any suitable number of retractor blades that can be placed into a collapsed configuration (for insertion into the target workspace) and an expanded configuration (for tissue manipulation). One or more blades can float (move independently from) other of the blades. On or more of the blades can be driven by (can receive torque transferred from) one of the other blades. As described herein, the multi-functional instruments can be driven by various drive components, such as combinations of motors, gears, actuators, transmission members, etc. Further, the multi-functional instruments described herein can include one or more cables (which act as tension members) that can be moved to actuate the end effector of a multi-functional MIS instrument to perform the various clinical functions and move with multiple degrees of freedom.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

As used herein, the term "target workspace" refers to anything within or pertaining to the endoscopic work cavity including the body of the patient, P, tissues and organs within the cavity, and tissue defining the cavity, and also to support structures for the MIS procedure including a cover and cannula supports, instruments and related attachments or medical implements including needles, suture materials, implants, meshes, etc. As used herein, the term "target tissue" refers to any tissue or organ that interacts with the target workspace including tissues and organs of the patient, P, natural tissues and organs introduced to the target workspace including natural transplant tissues and organs, artificial tissues and organs including mechanical or electromechanical organs, and tissue and organ assist devices such as pacemakers, mesh material, artificial skin and the like.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

A flexible part may have infinite degrees of freedom (DOF's). Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a serial arrangement of short, connected links as snake-like "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links having multiple DOFs, or an infinite-DOF link.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures were turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

As used herein, a surgical "retractor" or "retractor-type" clinical instrument refers to a medical instrument having contact surfaces that are configured to engage organs, tissues and/or portions of a surgical cavity or wound to thereby move, hold, lift, retain or otherwise interface with the target tissue and perform clinical retractor-type functions as appropriate for the surgical environment.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, California. Examples of such surgical systems are the da Vinci Xi® Surgical System (Model IS4000), da Vinci X® Surgical System (Model IS4200), and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled tool assembly 1400 (also referred to herein as a "tool") through a minimally invasive incision in the body or natural orifice of the patient P while the surgeon S views the surgical site and controls movement of the tool 1400 through control unit 1100.

An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of tools 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
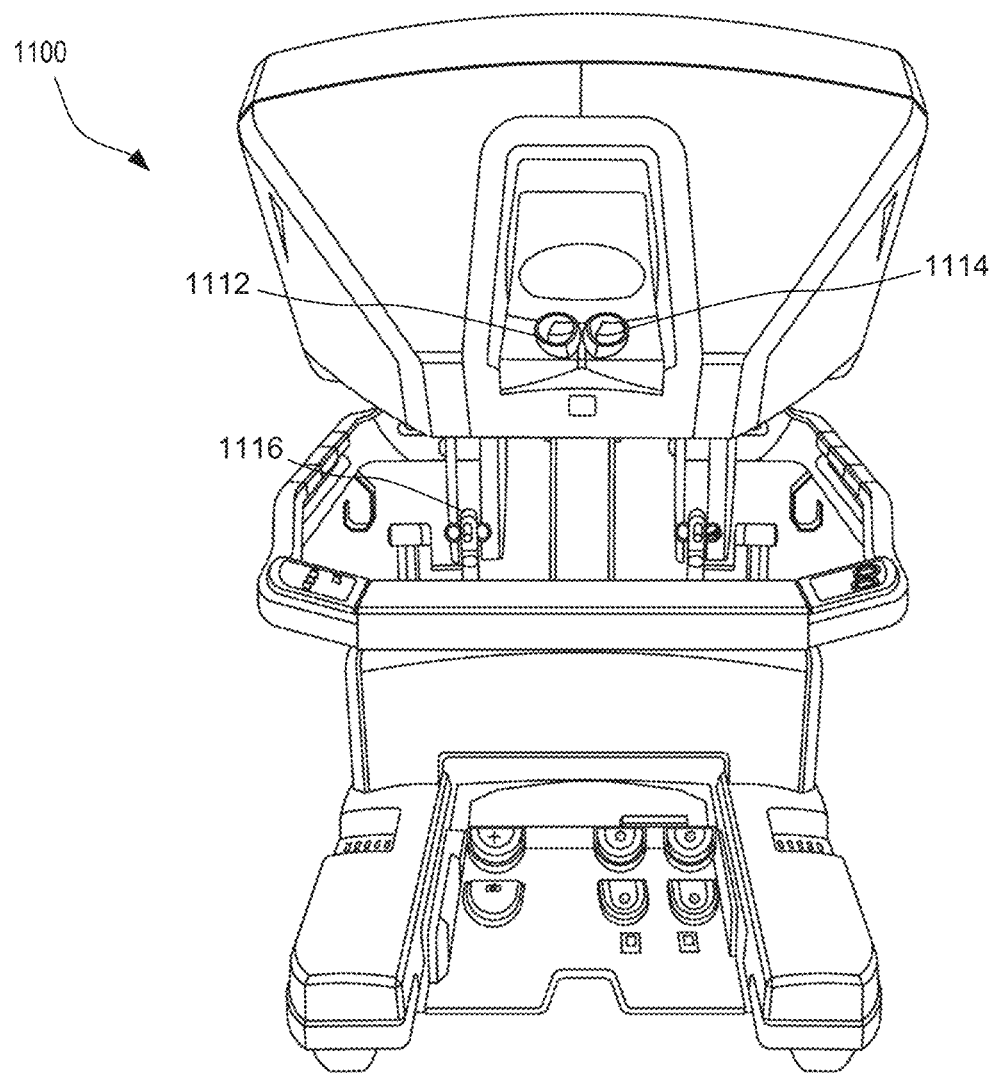
FIG. 2 is a perspective view of an optional auxiliary unit of the minimally invasive tele-operated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, and tactile feedback sensors (not shown) may be employed to transmit position, force, and tactile sensations from the instruments 1400 back to the surgeon's hands through the input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments however, the user control unit 1100 and the surgeon S can be in a different room, a completely different building, or other remote location from the patient allowing for remote surgical procedures.

Figure 3:
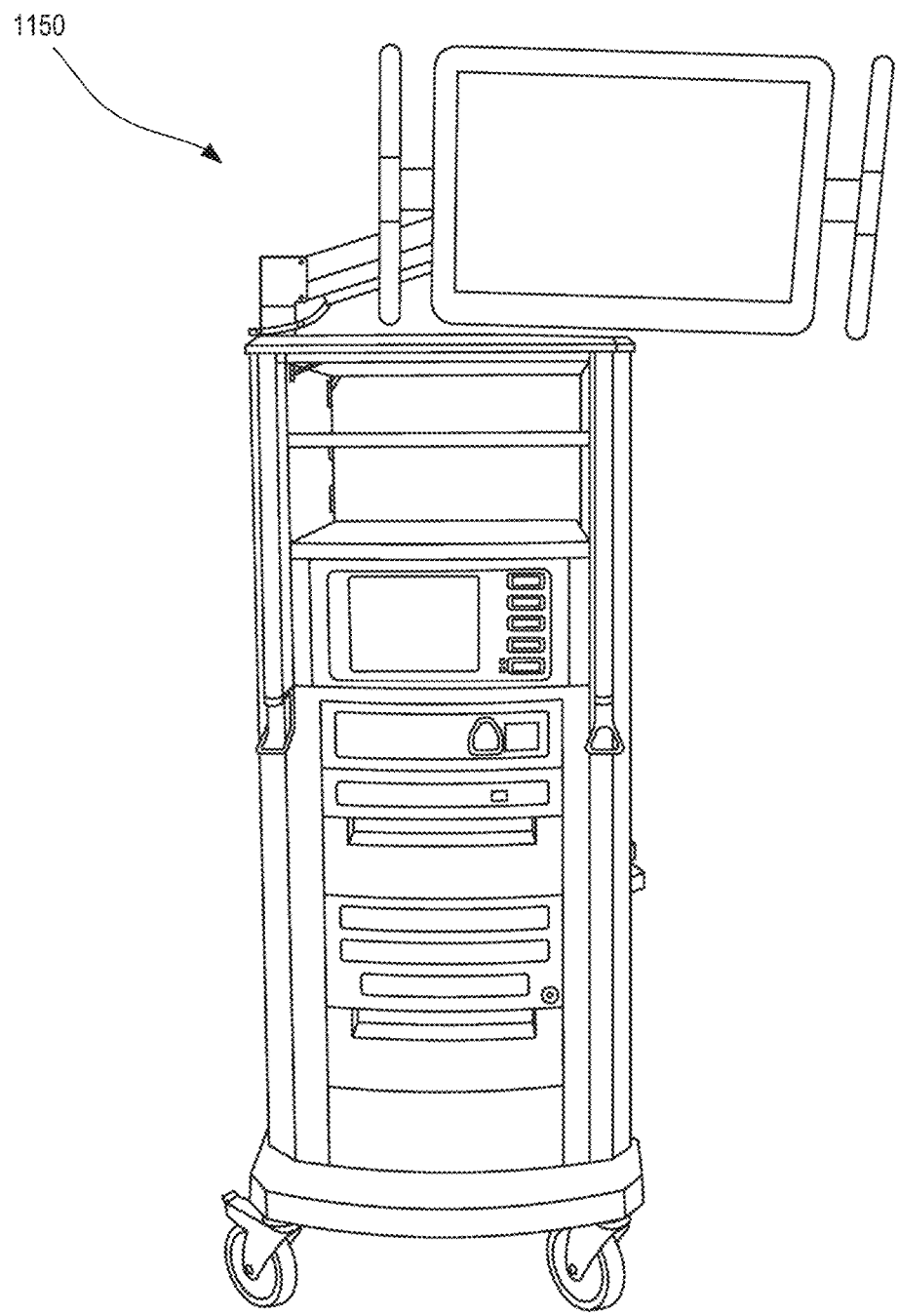
FIG. 3 is a perspective view of a user control console of the minimally invasive tele-operated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
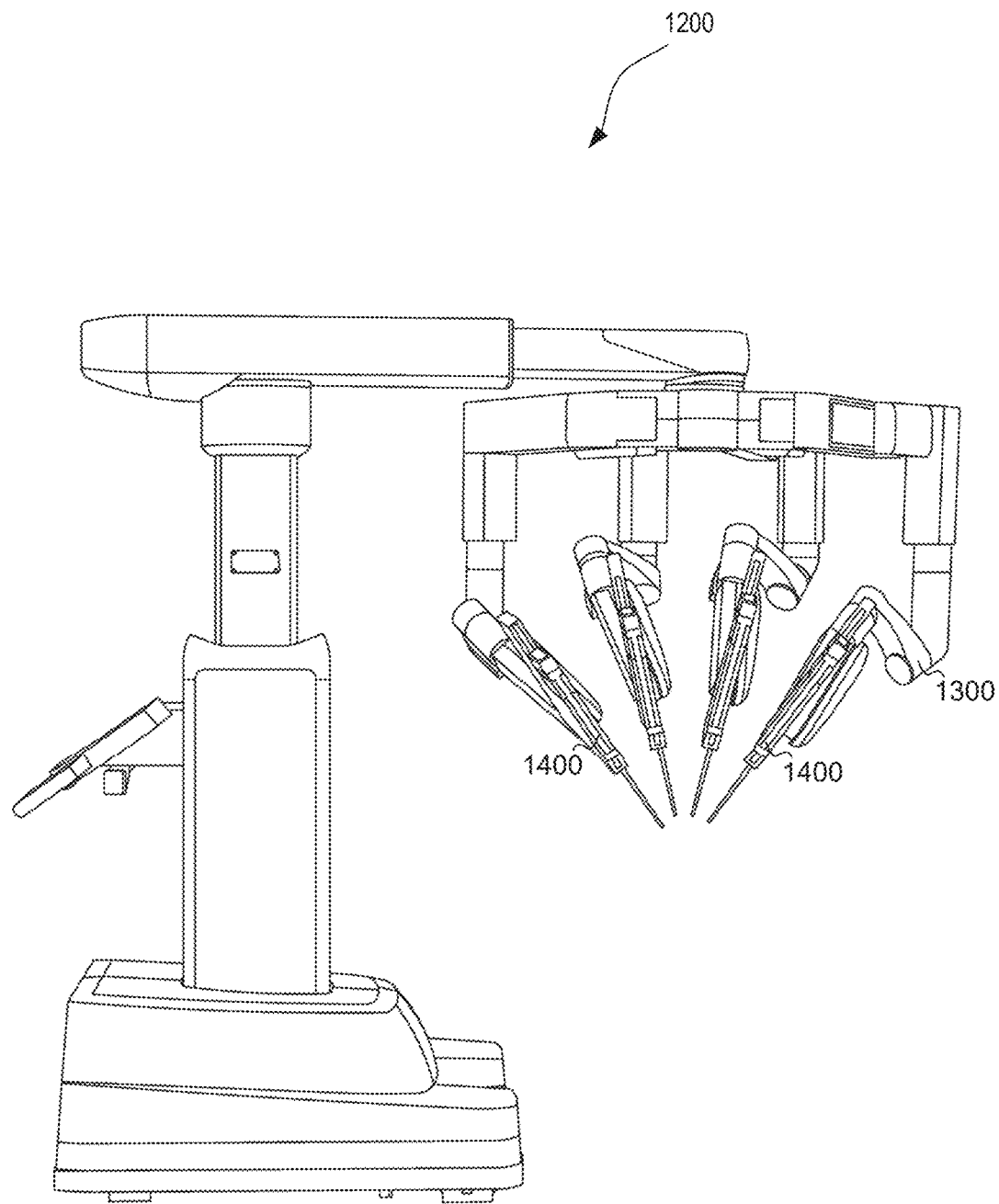
FIG. 4 is a front view of a manipulator unit, including a plurality of instruments, of the minimally invasive tele-operated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a kinematic remote center of motion is maintained at the incision or orifice. In this manner, the incision size can be minimized.

Many different clinical procedures can be performed using instruments 1400 operating through an incision or orifice in the patient P, which can interface with various objects while in the surgical environment within the patient. For example, an instrument 1400 can interface with tissue, organs, implant devices, surgical implements, as well as other instruments operating within the surgical environment. Many of these clinical procedures include using instruments to perform surgical retractor functions, such as moving, holding, lifting, retaining, or otherwise engaging tissue and organs. Such instruments can include blades or tool members designed to perform retractor functions, such as extendable surgical retractors and spreaders. FIGS. 5A-5E are diagrammatic illustrations of various portions of an instrument 2400, which functions as a retractor instrument, according to an embodiment. In some embodiments, the instrument 2400 or any of the components therein are optionally parts of a surgical system that performs minimally invasive surgical procedures, and which can include a manipulator unit, a series of kinematic linkages, a series of cannulas, or the like. The instrument 2400 (and any of the instruments described herein) can be used in any suitable surgical system, such as the MIRS system 1000 shown and described above and can be configured to perform tissue retraction or other processes.

The instrument 2400 includes a clevis 2610, a first tool member 2462 (which functions as a first retractor blade), a second tool member 2482 (which functions as a second retractor blade), and a tension member 2420. The clevis 2610 can be a part of or coupled to one or more kinematic linkages of the MIRS system 1000 as described above. For example, in some embodiments, the clevis 2610 can be directly coupled to a shaft (not shown). In other embodiments, the clevis 2610 can be rotatably coupled to a second kinematic link (not shown) to form a wrist assembly. As shown in FIGS. 5A and 5B, the clevis 2610 includes a connector 2680 to which the first retractor blade 2462 and the second retractor blade 2482 are rotatably coupled. Additionally, the clevis 2610 defines an axis A about which the first retractor blade 2462 and the second retractor blade 2482 can rotate, as described herein.

The first retractor blade 2462 and the second retractor blade 2482 together form an end effector 2460 that can be rotated about the axis A of the clevis 2610. As described herein, during certain operations, the end effector 2460 is configured such that the first retractor blade 2462 can rotate relative to the clevis while the second retractor blade 2482 remains in a fixed position, while in other operations rotation of the first retractor blade 2462 causes rotation of (i.e., drives) the second retractor blade 2482. As shown in FIGS. 5D, the first retractor blade 2462 has a proximal end portion 2467 and an opposite distal end portion 2463. The proximal end portion 2467 is movably coupled to the clevis 2610 by the connector 2680. The first retractor blade 2462 has a first tissue contact surface 2464 along its first side that functions to engage target tissue when the instrument 2400 performs retractor functions. The tissue contact surface 2464 can include any suitable features to facilitate interaction with tissue, such as, for example, fenestrations, protrusions (e.g., to improve tissue purchase), or curved surfaces. The first retractor blade 2462 includes a first coupling portion 2472 that is coupled to a second coupling portion 2492 of the second retractor blade 2482. The first coupling portion 2472 interacts with the second coupling portion 2492, as described herein, to produce the desired rotational movement of the second retractor blade 2482. The first coupling portion 2472 can be any suitable mechanism for coupling the first retractor blade 2462 to the second retractor blade 2482. For example, although shown as being a pin, in other embodiments, the first coupling portion 2472 can be a slot, an opening, a cable, a biasing member (e.g., a spring), or the like.

Figure 5C:
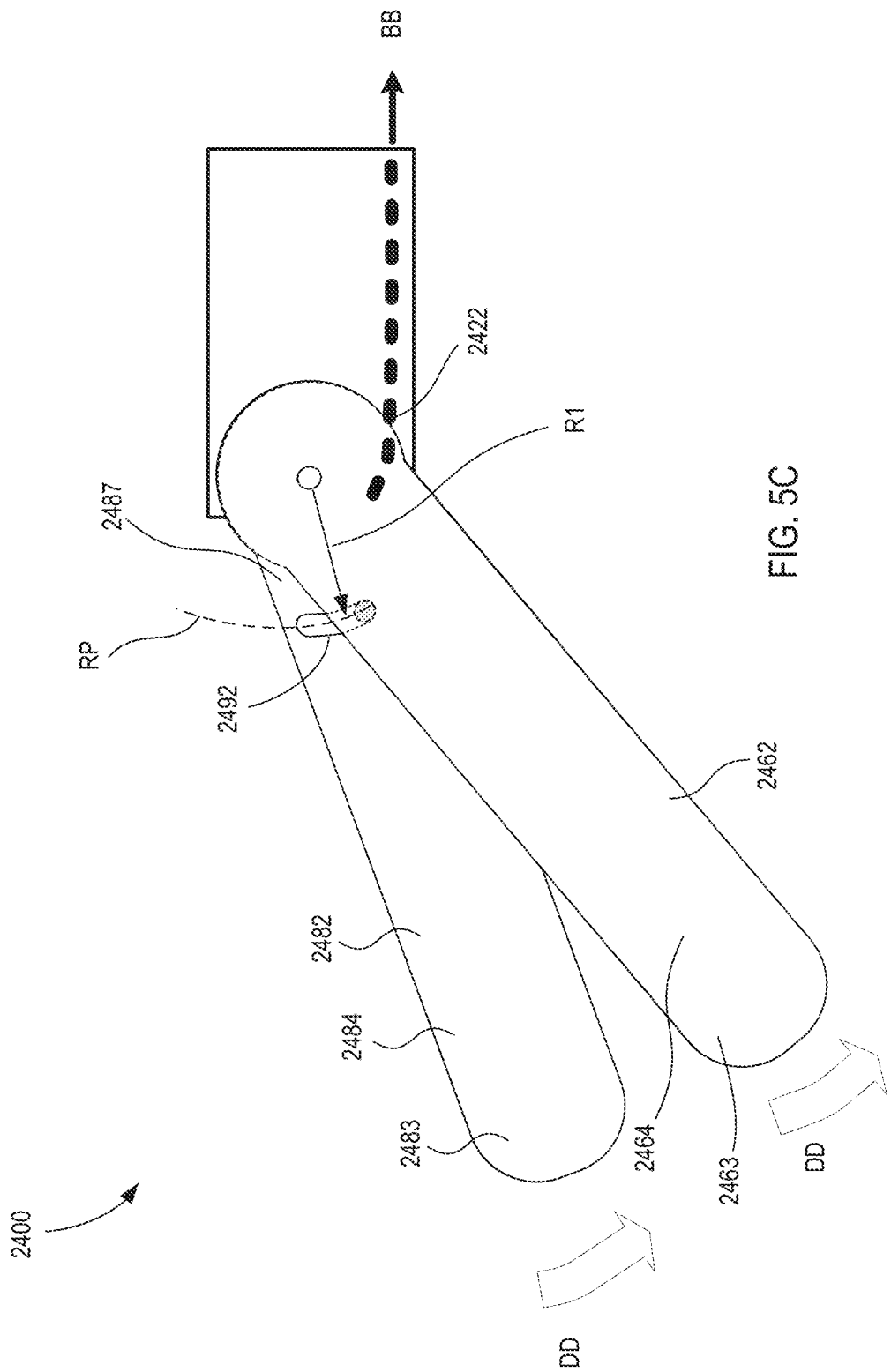

As shown in FIGS. 5A-5C, the tension member 2420 has a distal end portion 2422 coupled to the first retractor blade 2462. The distal end portion 2422 can be coupled to the first retractor blade 2462 at any suitable position and by any suitable method. For example, in some embodiments, the distal end portion 2422 of the tension member 2420 can be coupled to the proximal end portion 2467 of the first retractor blade 2462 by a pin or protrusion (not shown) that engages (or is received within) the first retractor blade 2462. In other embodiments, the distal end portion 2422 can be coupled to the first retractor blade 2462 via an adhesive. In yet other embodiments, the distal end portion 2422 of the tension member can be wrapped about a pulley portion of the first retractor blade 2462. The opposite proximal end portion of the tension member 2420 can be coupled to any suitable actuator (not shown, but which can function as a transmission) to move (or apply a torque to) the distal end portion 2422, as shown by arrow BB in FIGS. 5A and 5B. In some embodiments, the actuator of the instrument 2400 is motor driven and is thus suitable for a robotic or teleoperated surgical system. The tension member 2420 can be, for example, a cable, a cable/hypotube combination, a tension band, or any other suitable structure for applying a torque to the first retractor blade 2462.

As shown in FIGS. 5E, the second retractor blade 2482 has a proximal end portion 2487 and an opposite distal end portion 2483. The proximal end portion 2487 is movably coupled to the clevis 2610 by the connector 2680. The second retractor blade 2482 has a second tissue contact surface 2484 along its first side that functions to engage target tissue when the instrument 2400 performs retractor functions. The tissue contact surface 2484 can include any suitable features to facilitate interaction with tissue, such as, for example, fenestrations, protrusions (e.g., to improve tissue purchase), or curved surfaces. The second retractor blade 2482 includes a second coupling portion 2492 that is coupled to the first coupling portion 2472 of the first retractor blade 2462. The second coupling portion 2492 interacts with the first coupling portion 2472, as described herein, to produce the desired rotational movement of the second retractor blade 2482. The second coupling portion 2492 can be any suitable mechanism for coupling the first retractor blade 2462 to the second retractor blade 2482. For example, although shown as being a curved slot, in other embodiments, the second coupling portion 2492 can be a pin, a straight slot, an opening, a cable, a biasing member (e.g., a spring), or the like.

Referring to FIGS. 5A-5C, in use, the tension member 2420 applies a torque to the first retractor blade 2462, causing the first retractor blade 2462 rotate about the axis A, as shown by the arrows AA (FIG. 5A), CC (FIG. 5B), and DD (FIGS. 5B and 5C). Specifically, the first retractor blade 2462 can rotate relative to the clevis 2610 between a first orientation (FIG. 5A), a second orientation (FIG. 5B), a third orientation (FIG. 5C), and any other suitable orientations. Such orientations can include angular orientations between any of the first, second, or third orientation, as well as angular orientations outside (or beyond) those shown. The first retractor blade 2462 is directly driven by the tension member 2420. Said another way, the tension member 2420 is directly coupled to the first retractor blade 2462 such that movement of (or torque exerted by) the tension member 2420 produces movement of the first retractor blade 2462.

The second retractor blade 2482 is coupled to the first retractor blade 2462 such that it is indirectly moved by tension member 2420. Similarly stated, the second retractor blade 2482 is driven solely by the rotation of the first retractor blade 2462. This arrangement allows the end effector 2460 to be moved between various configurations by a single tension member (i.e., the tension member 2420) coupled to one of the blades. In some embodiments, the instrument 2400 can include additional tension members (not shown) that can be coupled to the first retractor blade 2462, the clevis 2610, or other portions of the instrument 2400. A second tension member can be used, for example, to cause movement of the first retractor blade 2462 in a direction opposite of that shown by the arrows AA, CC, and DD. In such embodiments, the second retractor blade 2482 is devoid of any attachment to the second tension member and remains driven solely by the rotation of the first retractor blade 2462.

To allow the end effector 2460 to move between a closed configuration (FIG. 5A) and one or more opened configurations (e.g., FIGS. 5B and 5C), the first coupling portion 2472 and the second coupling portion 2492 are configured such that the first retractor blade 2462 can selectively move the second retractor blade 2482. Specifically, the coupling portions are configured such that the second retractor blade 2482 remains in a fixed position relative to the clevis 2610 when the first retractor blade 2462 is between the first orientation (FIG. 5A) and the second orientation (FIG. 5B). Similarly stated, when the first retractor blade 2462 is angularly offset from the second retractor blade 2482 by less than a maximum offset angle $\theta$, the first retractor blade 2462 rotates independently from and does not drive the second retractor blade 2482. When the first retractor blade 2462 is between the second orientation (FIG. 5B) and the third orientation (FIG. 5C), however, continued rotation of the first retractor blade 2462 causes the second retractor blade 2482 to rotate, as shown by the arrow DD in FIG. 5C. Similarly stated, when the first retractor blade 2462 is angularly offset from the second retractor blade 2482 by the maximum offset angle $\theta$, the first retractor blade 2462 transfers at least a portion of the torque exerted by the tension member 2420 to the second retractor blade 2482 causing rotation of the second retractor blade 2482 about the axis A.

The first coupling portion 2472 and the second coupling portion 2492 can be any mechanisms that produce the selective engagement between the first retractor blade 2462 and the second retractor blade 2482 to cause the rotation described herein. For example, in some embodiments, the first coupling portion 2472 can move along a rotation path RP when the first retractor blade 2462 rotates relative to the clevis 2610. In some embodiments, the rotation path RP can be an arc having a constant radius. In other embodiments, the first coupling portion 2472 can move relative to the first retractor blade 2462, thereby producing a rotation path RP having a variable radius. For example, in some embodiments, the first coupling portion 2472 can include a protrusion that is movable coupled to the first retractor blade 2462 via a lever arm, a spring, or the like. Moreover, as shown in FIGS. 5B, 5C, and 5E, the second coupling portion 2492 can be an opening having a curved portion that is aligned with at least a portion of the rotation path RP. The curved portion can, for example, have a radius of curvature R1 that is the same a radius of at least a portion of the rotation path RP. In this manner, the first coupling portion 2472 can move within the second coupling portion 2492 during a portion of the rotation of the first retractor blade 2462 (i.e., when the angularly offset from the second retractor blade 2482 by less than the maximum offset angle $\theta$). This allows the first retractor blade 2462 to rotate independently from the second retractor blade 2482, and vice-versa. When the rotation path RP is no longer aligned with the curved portion of second coupling portion 2492, however, the first coupling portion 2472 engages a portion of the second retractor blade 2482 (e.g., a s side wall of the second connection portion 2492) and drives the second retractor blade as described herein.

In use, the instrument 2400 can initially be in a first (or closed) configuration in which the first retractor blade 2462 is aligned with the second retractor blade 2482 (see FIG. 5A). In the closed configuration, the first retractor blade 2462 is in its first orientation relative to the clevis 2610 and the offset angle $\theta$ between the first retractor blade 2462 and the second retractor blade 2482 is zero. When the instrument 2400 is in the closed configuration, the end effector 2460 can be advanced through a cannula (not shown) towards a surgical environment. The instrument 2400 can then be actuated (e.g., by applying a tension on the tension member 2420, as shown by the arrow BB) to move the instrument to one or more opened configurations for tissue retraction or other operations. Specifically, as described above, the first retractor blade 2462 can be rotated towards its second orientation, as shown by the arrows AA and CC. When the first retractor blade 2462 is between its first orientation (FIG. 5A) and its second orientation (FIG. 5B), the first retractor blade 2462 rotates independently from, and does not cause rotation of, the second retractor blade 2482. When the first retractor blade 2462 reaches its second orientation the offset angle between the first retractor blade 2462 and the second retractor blade 2482 reaches the maximum offset angle $\theta$. Thus, when the first retractor blade 2462 is between its first orientation and its second orientation, the instrument 2400 moves from the closed configuration to an opened configuration, in which the first retractor blade 2462 is spaced apart from (i.e., is "fanned out" from) the second retractor blade 2482. When the instrument is in an opened configuration, the retractor blades, and more specifically, the first tissue contact surface 2464 and the second tissue contact surface 2484 can engage, move, and manipulate tissue.

Referring to FIG. 5C, additional torque applied to the tension member 2420 (as shown by the arrow BB) causes the first retractor blade 2462 to be rotated towards its third orientation, as shown by the arrow DD. Because the offset angle between the first retractor blade 2462 and the second retractor blade 2482 is at the maximum offset angle $\theta$, further movement of the first retractor blade 2462 (in the same direction) produces concurrent rotation of the second retractor blade 2482. Said another way, the first retractor blade 2462 drives the second retractor blade 2482. This additional rotation of both retractor blades can be referred to as a yaw rotation. The instrument can be moved back towards the collapsed configuration by reversing the direction of rotation of the first retractor blade 2462.

The amount of the maximum angular offset between the first retractor blade 2462 and the second retractor blade 2482 can be adjusted by changing the dimensions of the first connection portion 2472 and the second connection portion 2492. For example, increasing the length of the opening can produce a larger rotation distance before the first retractor blade 2462 engages the second retractor blade 2482. Although the first connection portion 2472 is shown as being a pin that moves within a slot of the second connection portion 2492, in other embodiments, either of the blades can include a pin, a slot, or any other connection mechanism.

Although the instrument 2400 is shown and described as including two retractor blades and one tension member, in other embodiments, a retractor instrument can include any suitable number of retractor blades and tension members. For example, in some embodiments, an instrument can include three, four, or more retractor blades, with two of the retractor blades being drive blades that are on the outside (or end) of the remaining blades. Said another way, an instrument can include two drive blades each coupled to a tension member and one or more intermediate blades between the two drive blades that are driven by one or both of the drive blades. In some embodiments, the connection between the drive blades and the intermediate, driven blades can be such that the intermediate blades remain angularly centered between the two outer, drive blades when the instrument is transitioned from a closed configuration to an opened configuration. In this manner, the angular spacing between the blades can be controlled and maintained to ensure that there are no undesired gaps or spaces.

As one example, FIGS. 6A-6F are diagrammatic illustrations of various portions of an instrument 3400, which functions as a retractor instrument, according to an embodiment. In some embodiments, the instrument 3400 or any of the components therein are optionally parts of a surgical system that performs minimally invasive surgical procedures, and which can include a manipulator unit, a series of kinematic linkages, a series of cannulas, or the like. The instrument 3400 (and any of the instruments described herein) can be used in any suitable surgical system, such as the MIRS system 1000 shown and described above and can be configured to perform tissue retraction or other processes.

The instrument 3400 includes a clevis 3610, a first retractor blade 3462, a second retractor blade 3482, a third retractor blade 3562, a first tension member 3420, and a second tension member 3430. The clevis 3610 can be a part of or coupled to one or more kinematic linkages of the MIRS system 1000 as described above. For example, in some embodiments, the clevis 3610 can be directly coupled to a shaft (not shown). In other embodiments, the clevis 3610 can be rotatably coupled to a second kinematic link (not shown) to form a wrist assembly. As shown in FIGS. 6A, 6C, and 6D, the clevis 3610 includes a connector 3680 to which the retractor blades are rotatably coupled. Additionally, the clevis 3610 defines an axis A about which the first retractor blade 3462, the second retractor blade 3482, and the third retractor blade 3562 can rotate, as described herein.

Figure 6E:
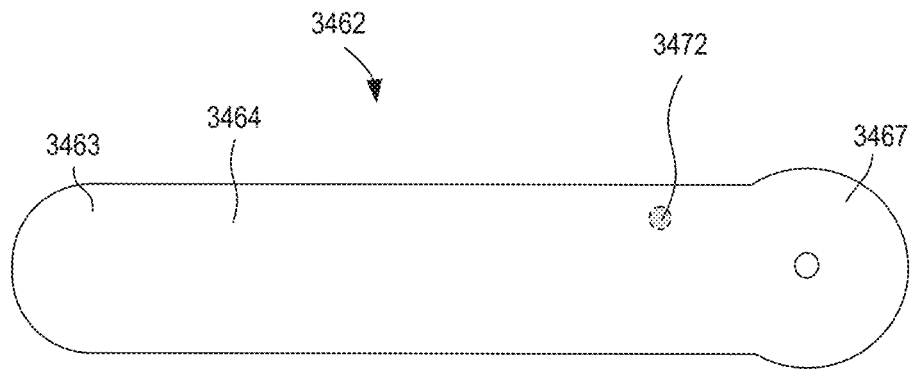
FIG. 6E is a diagrammatic view of a first blade shown in FIGS. 6A-6D.

The first retractor blade 3462, the second retractor blade 3482, and the third retractor blade 3562 together form an end effector 3460 that can be rotated about the axis A. The retractor blades are arranged such that the second retractor blade 3482 is between the first retractor blade 3462 and the third retractor blade 3562 (see FIGS. 6C and 6D). Similarly stated, the first retractor blade 3462 and the third retractor blade 3562 are the outer blades, and the second retractor blade 3482 is the inner blade, of the end effector 3460. As described herein, the end effector 3460 is configured such that the second retractor blade 3482 remains equally spaced (circumferentially) between the first retractor blade 3462 and the third retractor blade 3562 throughout a range of different opened configurations. As shown in FIGS. 6A and 6E, the first retractor blade 3462 has a proximal end portion 3467 and an opposite distal end portion 3463. The proximal end portion 3467 is movably coupled to the clevis 3610 by the connector 3680. The first retractor blade 3462 has a first tissue contact surface 3464 along its first side that functions to engage target tissue when the instrument 3400 performs retractor functions. The tissue contact surface 3464 can include any suitable features to facilitate interaction with tissue, such as, for example, fenestrations, protrusions (e.g., to improve tissue purchase), or curved surfaces. The first retractor blade 3462 includes a first coupling portion 3472 that is coupled to a second coupling portion 3492 of the second retractor blade 3482. The first coupling portion 3472 interacts with the second coupling portion 3492, as described herein, to produce the desired rotational movement of the second retractor blade 3482. The first coupling portion 3472 can be any suitable mechanism for coupling the first retractor blade 3462 to the second retractor blade 3482. For example, although shown as being a pin, in other embodiments, the first coupling portion 3472 can be a slot, an opening, a cable, a biasing member (e.g., a spring), or the like.

Figure 6F:
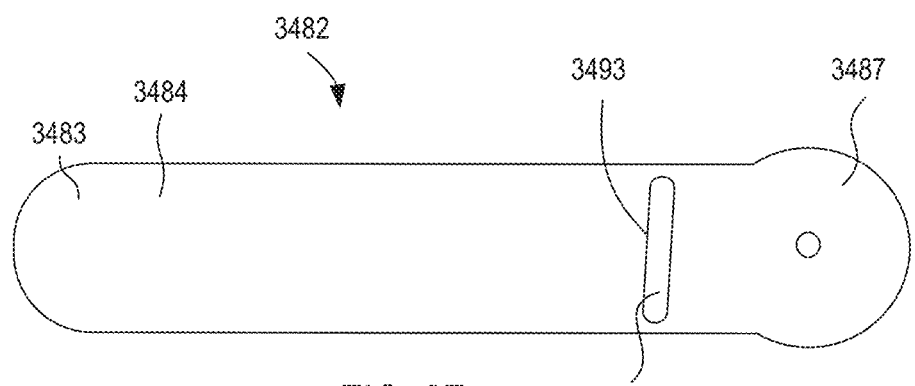
FIG. 6F is a diagrammatic view of a second blade shown in FIGS. 6A-6D.

As shown in FIGS. 6D, 6E, and 6F, the second (or intermediate) retractor blade 3482 has a proximal end portion 3487 and an opposite distal end portion 3483. The proximal end portion 3487 is movably coupled to the clevis 3610 by the connector 3680. The second retractor blade 3482 has a second tissue contact surface 3484 along its first side that functions to engage target tissue when the instrument 3400 performs retractor functions. The tissue contact surface 3484 can include any suitable features to facilitate interaction with tissue, such as, for example, fenestrations, protrusions (e.g., to improve tissue purchase), or curved surfaces. The second retractor blade 3482 includes a second coupling portion 3492 that is coupled to the first coupling portion 3472 of the first retractor blade 3462. The second retractor blade 3482 also includes a fourth coupling portion 3493 that is coupled to a third coupling portion 3572 of the third retractor blade 3562. The second coupling portion 3492 interacts with the first coupling portion 3472 and the fourth coupling portion 3493 interacts with the third coupling portion 3572 as described herein such that the second retractor blade 3482 remains equally spaced (circumferentially) between the first retractor blade 3462 and the third retractor blade 3562 throughout a range of different opened configurations. For example, FIG. 6B, shows an enlarged portion of the fourth coupling portion 3493, which includes a wall 3496 that defines a slot within which a pin of the third coupling portion 3572 (of the third retractor blade 3562) is disposed. In use, the pin of the third coupling portion 3572 can engage the wall 3496 (and similarly, the pin of the first coupling portion 3472 can engage a corresponding wall of the second coupling portion 3492) to transfer at least a portion of a torque from each of the first retractor blade 3462 and the third retractor blade 3562 to rotate the second retractor blade 3482 in a manner to remain equally spaced between the first and third retractor blades. The second coupling portion 3492 and the fourth coupling portion 3493 can be any suitable mechanism for coupling the first retractor blade 3462 and the third retractor blade 3562 to the second retractor blade 3482. For example, although shown as being a slot, in other embodiments, either or both of the second coupling portion 3492 and the fourth coupling portion 3493 can be a pin, an opening, a cable, a biasing member (e.g., a spring), or the like.

As shown in FIGS. 6C and 6D, the third retractor blade 3562 has a proximal end portion 3567 and an opposite distal end portion 3563. The proximal end portion 3567 is movably coupled to the clevis 3610 by the connector 3680. The third retractor blade 3562 has a first tissue contact surface 3564 along its first side that functions to engage target tissue when the instrument 3400 performs retractor functions. The tissue contact surface 3564 can include any suitable features to facilitate interaction with tissue, such as, for example, fenestrations, protrusions (e.g., to improve tissue purchase), or curved surfaces. The third coupling portion 3572 of the third retractor blade 3562 is coupled to the fourth coupling portion 3493 of the second retractor blade 3482, as described above. The third coupling portion 3572 can be any suitable mechanism for coupling the third retractor blade 3562 to the second retractor blade 3482. For example, although shown as being a pin, in other embodiments, the first coupling portion 3472 can be a slot, an opening, a cable, a biasing member (e.g., a spring), or the like.

As shown in FIGS. 6A, 6C, and 6D, the first tension member 3420 has a distal end portion 3422 coupled to the first retractor blade 3462 and the second tension member 3430 has a distal end portion 3432 coupled to the third retractor blade 3562. The distal end portion 3422 can be coupled to the first retractor blade 3462 and the distal end portion 3432 can be coupled to the third retractor blade 3562 at any suitable position and by any suitable method. For example, in some embodiments, the distal end portion 3422 can be coupled to the first retractor blade 3462 and the distal end portion 3522 can be coupled to the third retractor blade 3562 by a pin or protrusion (not shown) that engages (or is received within) the retractor blade. In other embodiments, the distal end portions 3422, 3432 can be coupled to their respective retractor blades via an adhesive. In yet other embodiments, the distal end portions 3422, 3432 can be wrapped about a pulley portion of the retractor blade. The opposite proximal end portions of the tension member 3420 and the tension member 3430 can be coupled to any suitable actuator (not shown, but which can function as a transmission) to move (or apply a torque to) the distal end portion 3422 and the distal end portion 3432 as shown by arrows EE and FF in FIGS. 6C and 6D. In some embodiments, the actuator of the instrument 3400 is motor driven and is thus suitable for a robotic or teleoperated surgical system. The tension members 3420, 3430 can be, for example, a cable, a cable/hypotube combination, a tension band, or any other suitable structure for applying a torque to the first retractor blade 3462.

Referring to FIGS. 6A-6D, in use, the tension member 3420 applies a torque to the first retractor blade 3462, causing the first retractor blade 3462 rotate about the axis A, as shown by the arrows GG (FIG. 6C) and HH (FIG. 6D). The tension member 3430 applies a torque to the third retractor blade 3562, causing the third retractor blade 3562 to maintain its angular position (as shown in FIGS. 6C and 6D), rotate about the axis A in a direction opposite that of the first retractor blade 3462, or to controllably allow rotation of the third retractor blade 3562 in the same direction as that of the first retractor blade 3462. In this example, the first retractor blade 3462 is shown as rotating relative to the clevis 3610 between multiple different angular orientation (FIGS. 6A, 6C, and 6D), while the third retractor blade 3562 is maintained in a constant orientation. The retractor blades, however, can be rotated between and to any other suitable orientations, including angular orientations between any of the first, second, or third orientation, as well as angular orientations outside (or beyond) those shown. The second retractor blade 3482 is coupled first retractor blade 3462 and the third retractor blade 3562 such that it is indirectly moved by either or both of the tension member 3420 and the tension member 3430. Similarly stated, the second retractor blade 3482 is driven solely by the rotation either or both of the first retractor blade 3462 and the third retractor blade 3562.

To allow the end effector 3460 to move between a closed configuration (FIG. 6A) and one or more opened configurations (e.g., FIGS. 6C and 6D), the first coupling portion 3472, the second coupling portion 3492, the third coupling portion 3572, and the fourth coupling portion 3493 are configured such that the second retractor blade 3482 is moved by and remains centered between the first retractor blade 3462 and the third retractor blade 3562. Similarly stated, the coupling portions are configured such that when the first retractor blade 3462 is in a first angular orientation and the third retractor blade 3562 is in a third angular orientation, the second retractor blade 3482 is in a second angular orientation that is centered between the first angular orientation and the third angular orientation. For example, the instrument 3400 can initially be in a first (or closed) configuration in which the retractor blades are aligned (see FIG. 6A). Said another way, when the instrument 3400 is in the closed configuration, a first center line $CL_1$ of the first retractor blade 3462, a second center line $CL_2$ of the second retractor blade 3482, and a third center line $CL_3$ of the third retractor blade 3562 are coaxial. In the closed configuration, each of the retractor blades are in the same angular orientation, and the angle between the center lines is zero. When the instrument 3400 is in the closed configuration, the end effector 3460 can be advanced through a cannula (not shown) towards a surgical environment.

The instrument 3400 can then be actuated, for example, by applying a tension on the tension member 3420, as shown by the arrow EE and/or the tension member 3430, as shown by the arrow FF to move the instrument to one or more opened configurations (e.g., FIGS. 6C and 6D) for tissue retraction or other operations. The first retractor blade 3462 can be rotated towards a first orientation, as shown by the arrow GG in FIG. 6C, to place the instrument 3400 (and the end effector 3460) into a first opened configuration. When the instrument 3400 is in the first opened configuration (FIG. 6C), the second retractor blade 3482 is in a second orientation, and the third retractor blade 3562 is in a third orientation. Additionally, the first center line $CL_1$ is offset from the second center line $CL_2$ by an offset angle $\alpha_1$ and the third center line $CL_3$ is offset from the second center line $CL_2$ by an offset angle $\beta_1$. The first retractor blade 3462 can be rotated further towards a fourth orientation, as shown by the arrow HH in FIG. 6D, to place the instrument 3400 (and the end effector 3460) into a second opened configuration. When the instrument 3400 is in the second opened configuration (FIG. 6D), the second retractor blade 3482 is in a fifth orientation, and the third retractor blade 3562 is in a sixth orientation. Although FIGS. 6C and 6D show the sixth orientation being the same as the third orientation, it is understood that the third retractor blade 3562 need not remain at a constant angular orientation. Additionally, when the instrument 3400 is in the second opened configuration (FIG. 6D), the first center line $CL_1$ is offset from the second center line $CL_2$ by an offset angle $\alpha_2$ and the third center line $CL_3$ is offset from the second center line $CL_2$ by an offset angle $\beta_2$. The connection portions are configured such that the offset angle $\alpha_1$ is substantially the same as the offset angle $\beta_1$ and the offset angle $\alpha_2$ is substantially the same as the offset angle $\beta_2$. Similarly stated, when the instrument 3400 is in the first opened configuration, the second angular orientation of the second retractor blade 3582 is centered between the first angular orientation of the first retractor blade 3462 and the third angular orientation of the third retractor blade 3562. Moreover, when the instrument 3400 is in the second opened configuration, the fifth angular orientation of the second retractor blade 3582 is centered between the fourth angular orientation of the first retractor blade 3462 and the sixth angular orientation of the third retractor blade 3562.

Similar to the instrument 2400 described above, the second retractor blade 3482 is driven solely by the rotation of the first retractor blade 3462, the third retractor blade 3562, or both. Additionally, the second retractor blade 3482 is driven in a manner that maintains the second retractor blade 3482 centered between the first retractor blade 3462 and the third retractor blade 3562. Specifically, when a first torque is applied by the first tension member 3420 to the first retractor blade 3462, a portion of the first torque is transferred to the second retractor blade 3482 by the interface between the first coupling portion 3472 and the second coupling portion 3492. Similarly, when a second torque is applied by the second tension member 3430 to the third retractor blade 3562, a portion of the second torque is transferred to the second retractor blade 3482 by the interface between the third coupling portion 3572 and the fourth coupling portion 3493. In some operations, the direction of the first torque is opposite the direction of the second torque (i.e., to cause the end effector 3460 to move to an opened configuration). In some embodiments, the coupling portions are configured such that the portion of the first torque transferred to the second retractor blade 3482 and the portion of the second torque transferred to the second retractor blade 3482 are equal. In other embodiments, the coupling portions are configured such that the portion of the first torque transferred to the second retractor blade 3482 and the portion of the second torque transferred to the second retractor blade 3482 are within ten percent of each other. In this manner, the second retractor blade 3482 can remain centered between the first retractor blade 3462 and the third retractor blade 3562.

Figure 6G:
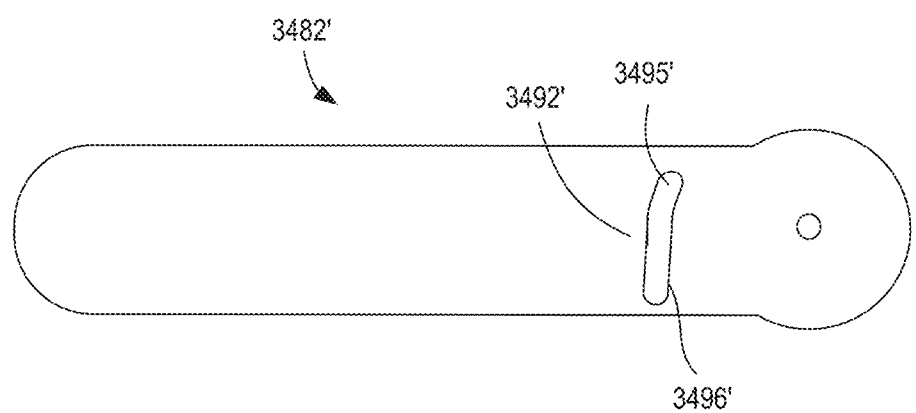
FIG. 6G is a diagrammatic view of a blade according to an embodiment that can be included in the instrument shown in FIGS. 6A-6D.

In some embodiments, the coupling portions can be configured such that the relative motion between the mating portions is balanced to produce substantially equal transfer of torque to the second retractor blade 3482. For example, in some embodiments, the first coupling portion 3472 can move along a first rotation path and the third coupling portion 3572 can move along a second rotation path (which can, in some instances, be aligned with the first rotation path). The second coupling portion 3492 can be within the first rotation path and the fourth coupling portion 3493 can be within the second rotation path such that the engagement between the coupling portions produces substantially equal torque transfer to the second retractor blade 3482. For example, in some embodiments, the second coupling portion 3492 and the fourth coupling portion 3493 can be a slot that is at least partially aligned with rotation paths of the first coupling portion 3472 and the third coupling portion 3572. In some embodiments, the slot can be linear. In other embodiments, the slot can be curved, similar to the coupling portion 2492 shown and described above. In yet other embodiments, the slot can include both a linear portion and a curved portion. For example, in some embodiments a retractor blade according to an embodiment can include a connection portion having a slot that has a linear portion and a curved portion. FIG. 6G shows a retractor blade 3482' according to an embodiment that has a connector portion 3492'. As shown, the connector portion 3492' defines a slot having a linear portion 3496' and a curved portion 3495'.

The instrument 2400, the instrument 3400, and any of the instruments described herein can be included in any suitable kit and can be used to perform variety of surgical methods. For example, in some embodiments, the instrument 2400 can be included in a surgical kit that includes, among other items, alternative instruments (e.g., the instrument 3400, or other multi-blade instruments), and one or more support devices (not shown) that can enhance the tissue manipulating capability of the instruments. Such support devices can be any of the support devices shown and described in Provisional Application No. 62/767,682, entitled "Support Apparatus for a Medical Retractor Device," filed on November 15, 2018, which is incorporated herein by reference in its entirety.

Figure 7:
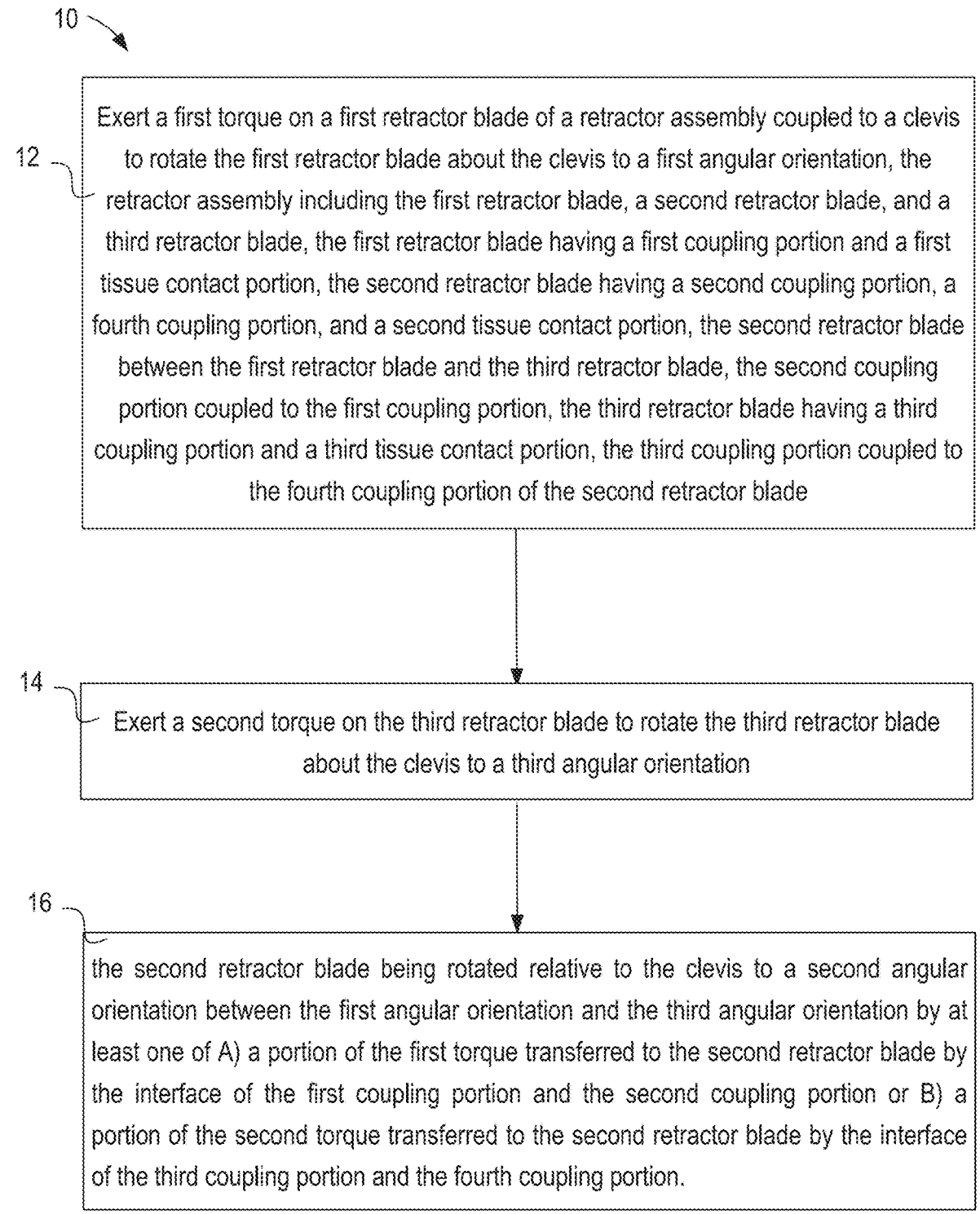
FIG. 7 is a flow chart showing a method of manipulating an instrument according to an embodiment.

FIG. 7 is flow chart method 10 of using a retractor instrument, according to an embodiment. Although the method 10 is described along with FIGS. 6A-6D as being performed with the instrument 3400, in other embodiments, the method 10 (and any of the methods described herein) can be performed using any of the devices described herein. Referring to FIG. 7, the method 10 includes exerting, at 12, a first torque on a first retractor blade of a retractor assembly coupled to a clevis to rotate the first retractor blade about the clevis to a first angular orientation. The retractor assembly can be, for example, the instrument 3400 and includes the first retractor blade 3462, the second retractor blade 3482, and the third retractor blade 3562. The first retractor blade has a first coupling portion and a first tissue contact portion, the second retractor blade has a second coupling portion, a fourth coupling portion, and a second tissue contact portion. The third retractor blade has a third coupling portion and a third tissue contact portion. The second retractor blade is between the first retractor blade and the third retractor blade. Specifically, the second coupling portion is coupled to the first coupling portion, and the third coupling portion is coupled to the fourth coupling portion. The first torque can be applied by any suitable mechanism, such as, for example by a tension member. Movement of the first retractor blade is illustrated, for example, by the movement of the first retractor blade 3462 shown in FIGS. 6C and 6D.

The method further includes exerting, at 14, a second torque on the third retractor blade to position the third retractor blade about the clevis in a third angular orientation. The second torque can be applied by any suitable mechanism, such as, for example by a tension member. Positioning of the third retractor blade can be accomplished, for example, by maintaining the third retractor blade in a constant position (as shown in FIGS. 6C and 6D) or by rotating the third retractor blade about the clevis. In some embodiments, the exerting the first torque and the exerting the second torque are performed at the same time.

In response to the exerting the first torque and the exerting the second torque, the second retractor blade is rotated relative to the clevis to a second angular orientation between the first angular orientation and the third angular orientation. Specifically, as described herein, the second retractor blade is rotated by at least one of A) a portion of the first torque transferred to the second retractor blade by the interface of the first coupling portion and the second coupling portion or B) a portion of the second torque transferred to the second retractor blade by the interface of the third coupling portion and the fourth coupling portion. In some embodiments, the second angular orientation is centered between the first angular orientation and the third angular orientation.

In some embodiments, the method 10 and any other methods described herein can be performed in connection with any suitable procedure, such as, for example, a nipple sparing mastectomy or any other suitable procedure.

Although the instrument 2400 is shown as having two blades and the instrument 3400 is shown as having three blades, in other embodiments an instrument can include any number of tool members that function as retractor blades.

For example, in some embodiments, an instrument can include multiple intermediate blades between a pair of outer blades. The intermediate blades can be driven by the outer blades (as described above in connection with the instrument 2400), maintained in a centered position between the outer blades (as described above in connection with the instrument 3400), or both. One example of an instrument that includes a pair of outer blades that drives the inner blades is shown in FIGS. 8-16, which show an instrument 4400 according to an embodiment. The instrument 4400 (and any of the instruments described herein) can be used in any suitable surgical system, such as the MIRS system 1000 shown and described above. The instrument 4400 includes a transmission assembly 4700 (that can function as an actuator mechanism or transmission mechanism), an instrument shaft 4410, a wrist assembly 4500, and an end effector 4460.

Figure 9:
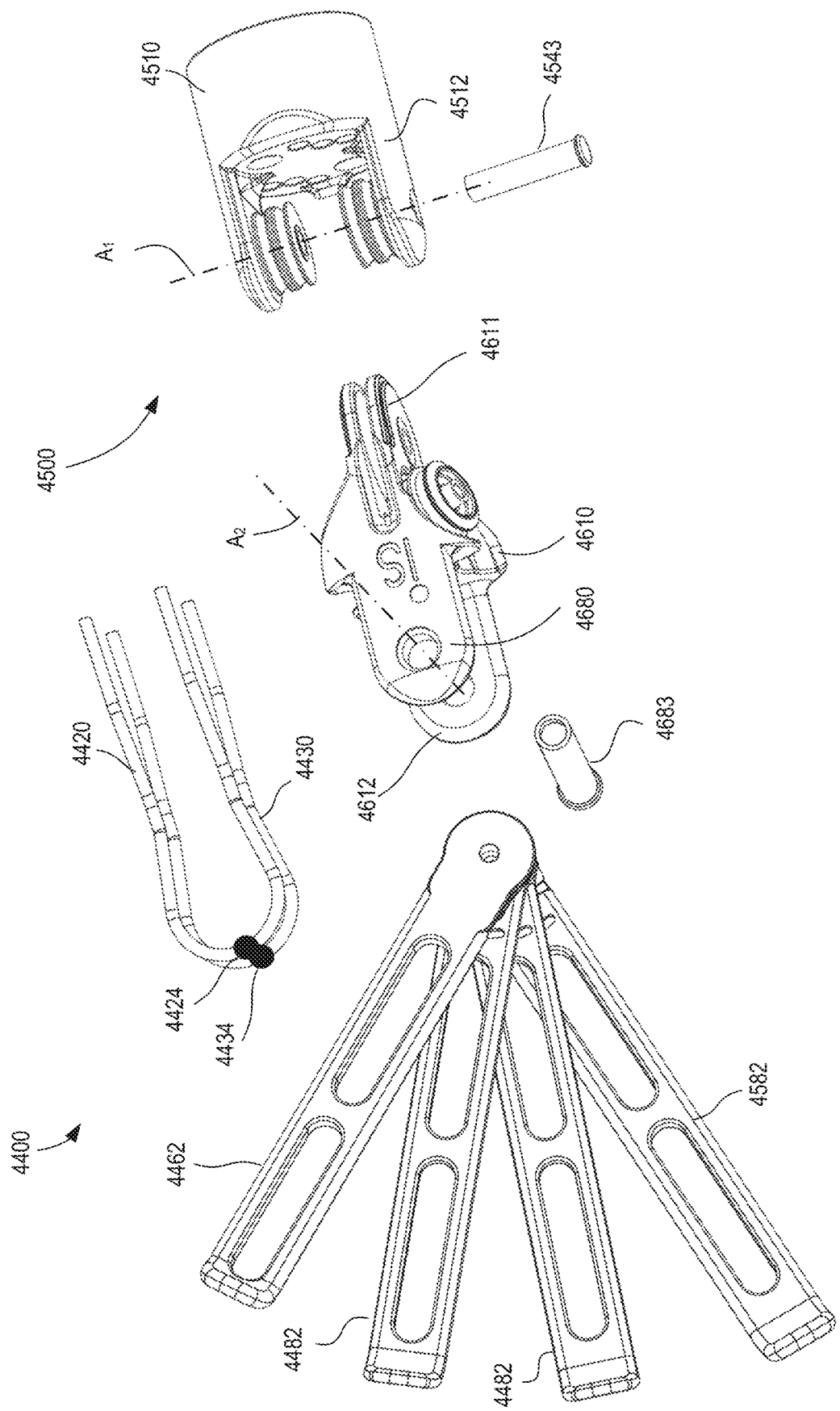
FIG. 9 is an enlarged exploded perspective view of a distal end portion of the instrument in the first orientation indicated by the region Z shown in FIG. 8A.
Figure 10:
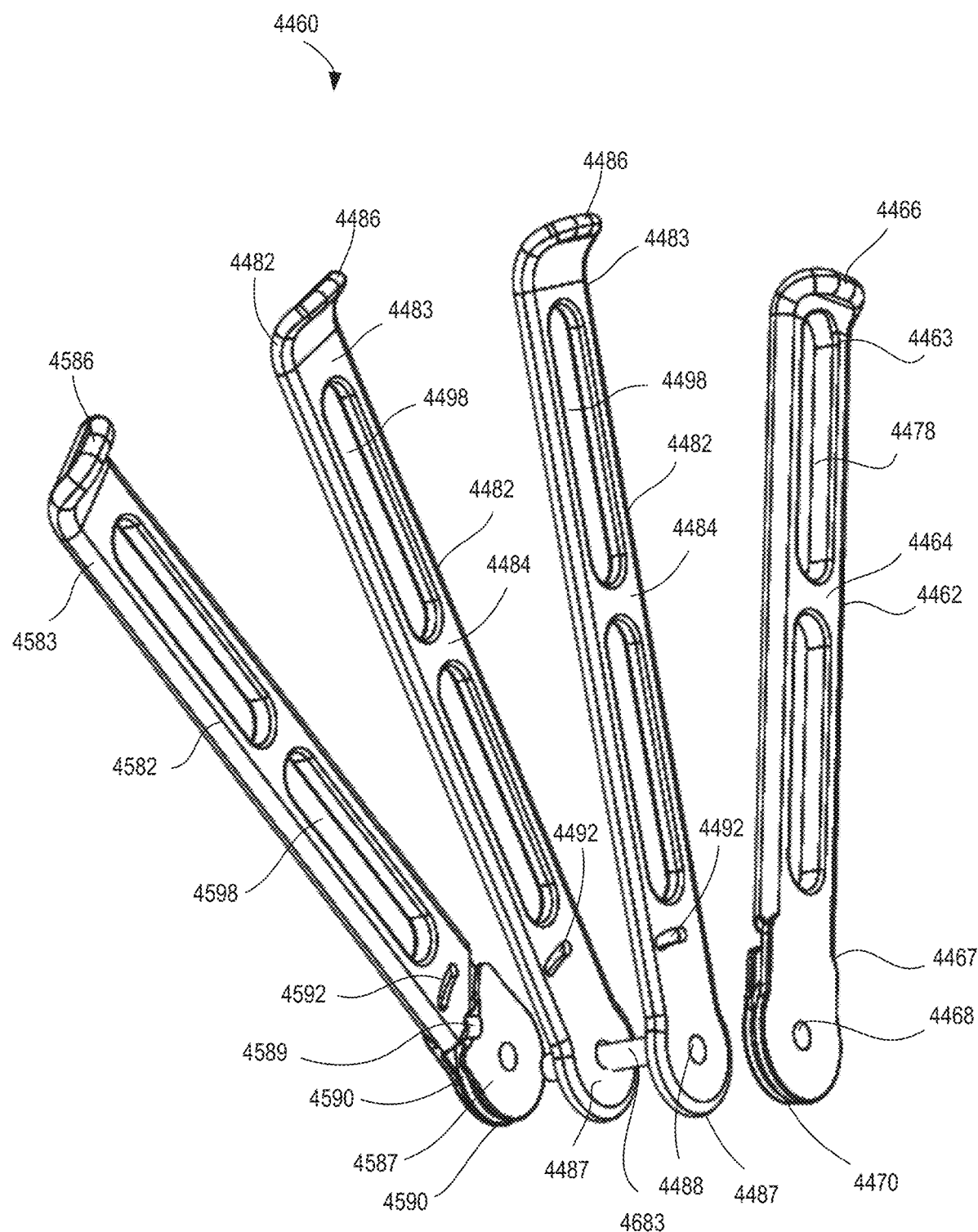
FIGS. 10-12 are perspective views of the retractor blades of the instrument shown in FIGS. 8 and 9, showing a first side of the retractor blades (FIGS. 10 and 12) and a second side of the retractor blades (FIG. 11).
Figure 11:
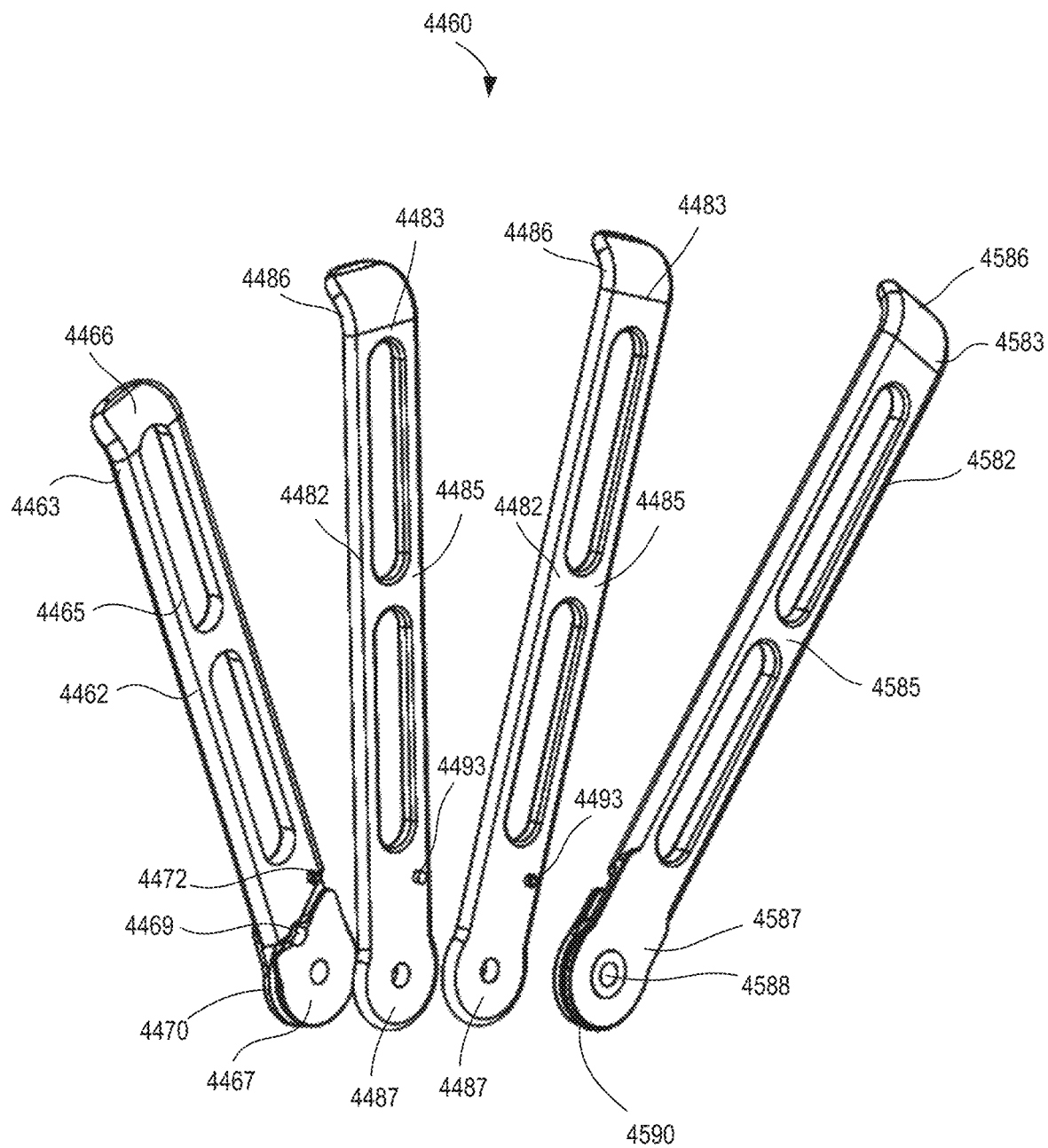
Figure 12:
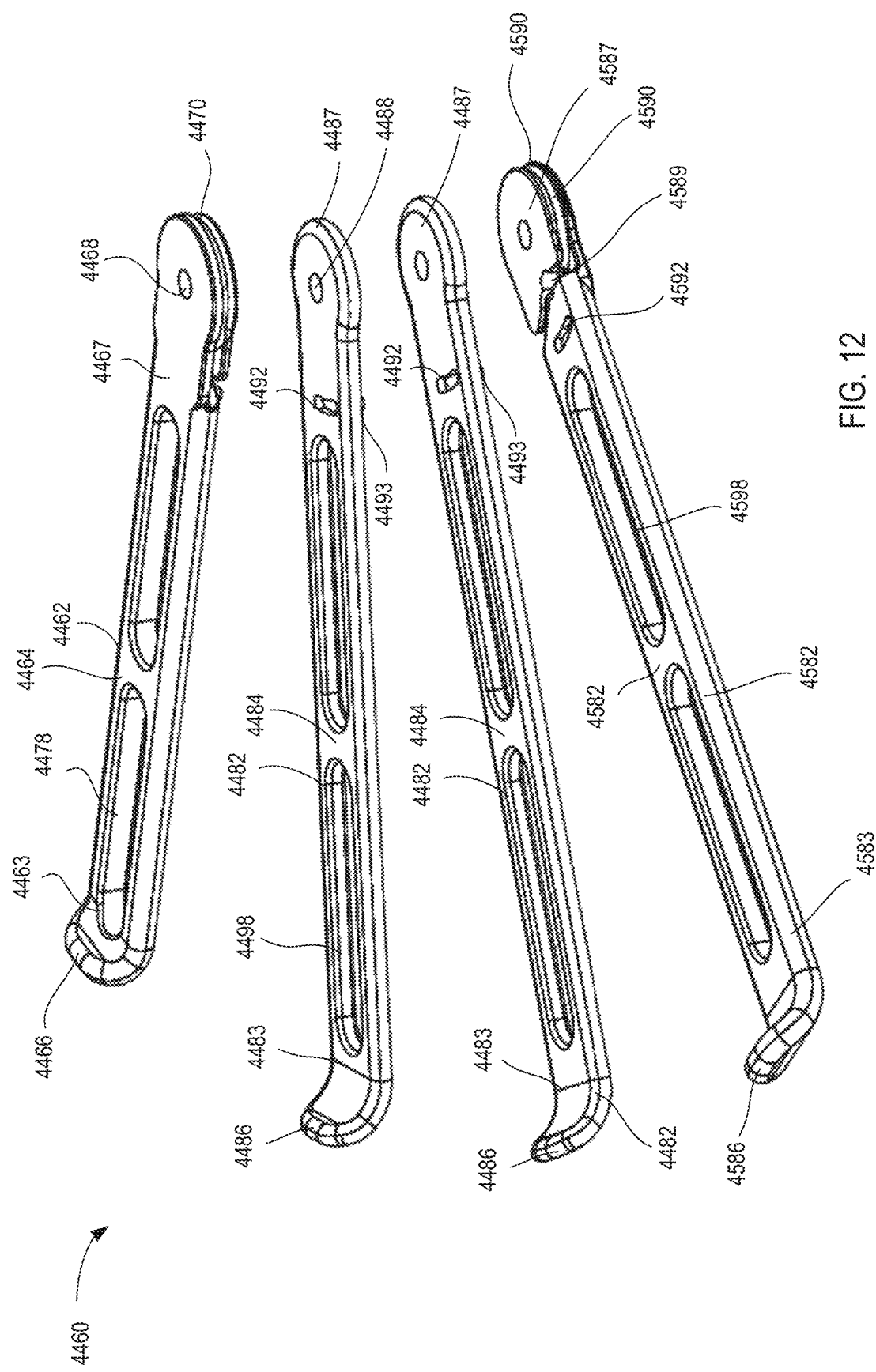
Figure 16:
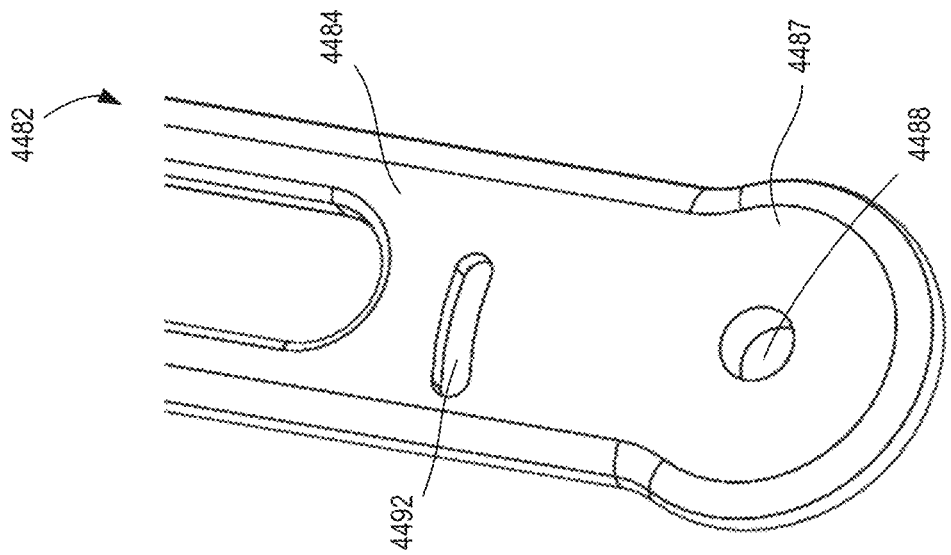
FIGS. 15 and 16 are perspective views of a proximal end portion of a second retractor blade of the instrument shown in FIGS. 8 and 9, showing a first side (FIG. 15) and a second side (FIG. 16).
Figure 15:
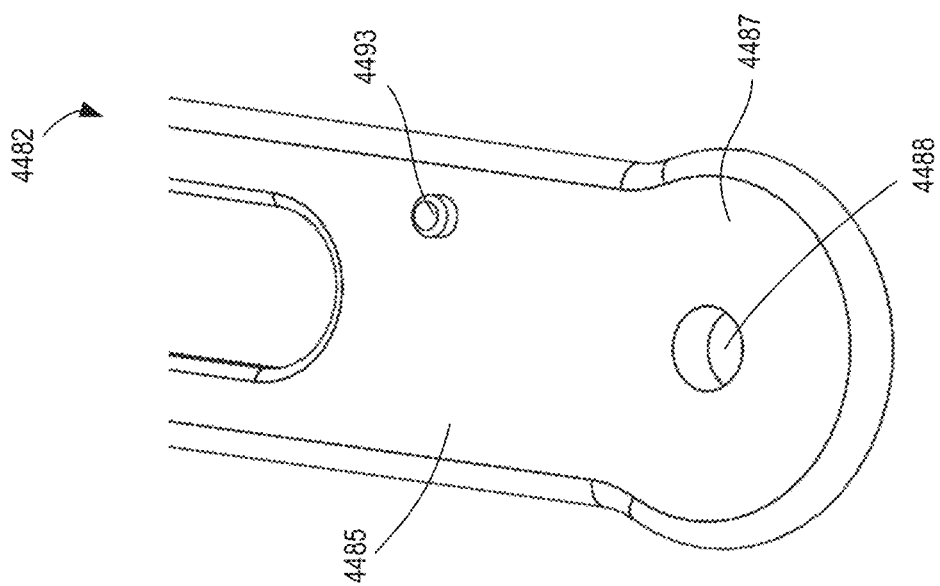

The instrument 4400 includes at least a first tension member 4420 and a second tension member 4430 that couple the transmission mechanism 4700 to the outer retractor blades of the end effector 4460. The tension members have been omitted in certain figures to show more clearly various features pertaining to the rotatable retractor blades of the end effector 4460. Referring to FIG. 9, the first tension member 4420 is coupled to the first retractor blade 4462 and the second tension member 4430 is coupled to the third retractor blade 4582. The instrument 4400 is configured such that movement of the first tension member 4420 and the second tension member 4430 can produce a yaw rotation of the end effector 4460 about a second axis of rotation $A_2$, grip rotation of the retractor blades of the end effector 4460 about the yaw axis, or any combination of these movements. In some embodiments, the instrument 4400 is configured such that movement of the first tension member 4420 and the second tension member 4430 can also produce rotation of the wrist assembly 4500 (i.e., pitch rotation) about a first axis of rotation, $A_1$. In other embodiments, the instrument 4400 can include additional tension members (not shown) that separately change the pitch of the instrument 4400.

The transmission 4700 produces movement of each of the first tension member 4420 and the second tension member 4430 to produce the desired movement (pitch, yaw, or grip) at the wrist assembly 4500. Specifically, the transmission 4700 includes components and controls to move some of the tension members in a proximal direction (i.e., to pull in certain tension members) while simultaneously allowing the distal movement (i.e., releasing or "paying out") of other of the tension members. In this manner, the transmission 4700 can maintain the desired tension within the tension members, and, in some embodiments, can ensure that the lengths of the tension members are conserved (i.e., moved in equal amounts) during the entire range of motion of the wrist assembly 4500. In some embodiments, for example, the transmission assembly 4700 can be any of the transmission assemblies shown and described in International Patent Application No. PCT/US2017/062258, (filed Nov. 14, 2017), entitled "Cable Length Conserving Medical Instrument," which is incorporated herein by reference in its entirety. In other embodiments however, conservation of the lengths of the tension members is not required.

In some embodiments, the transmission mechanism 4700 can include one or more linear actuators that produce translation (linear motion) of a portion of the tension members. Such transmission mechanisms can include, for example, a gimbal, a lever, or any other suitable mechanism to directly pull (or release) an end portion of any of the tension members. For example, in some embodiments, the transmission mechanism 4700 can include any of the transmission assemblies or components described in U.S. Patent Application Pub. No. US 2015/0047454 A1 (filed Aug. 15, 2014), entitled "Lever Actuated Gimbal Plate," or U.S. Pat. No. 6,817,974 B2 (filed Jun. 28, 2001), entitled "Surgical Tool Having Positively Positionable Tendon-Actuated Multi-Disk Wrist Joint," each of which is incorporated herein by reference in its entirety. In other embodiments, however, the transmission mechanism 4700 can include a capstan or other motor-driven roller that rotates or "winds" a portion of any of the tension members to produce the desired tension member movement. For example, in some embodiments, the backend mechanism 4700 can include any of the backend assemblies or components described in U.S. Pat. No. 9,204,923 B2 (filed Jul. 16, 2008), entitled "Medical Instrument Electronically Energized Using Drive Cables," which is incorporated herein by reference in its entirety.

The shaft 4410 can be any suitable elongated shaft that couples the wrist assembly 4500 to the transmission mechanism 4700. Specifically, the shaft 4410 includes a proximal end portion 4411 that is coupled to a housing of the backend mechanism 4700, and a distal end portion 4412 that is coupled to the wrist assembly 4500. The shaft 4410 defines a passageway or series of passageways through which the tension members and other components (e.g., electrical wires, ground wires, or the like) can be routed from the transmission mechanism 4700 to the wrist assembly 4500. Although shown as being cylindrical, in other embodiments the shaft 4410 can have any suitable shape.

Figure 8:
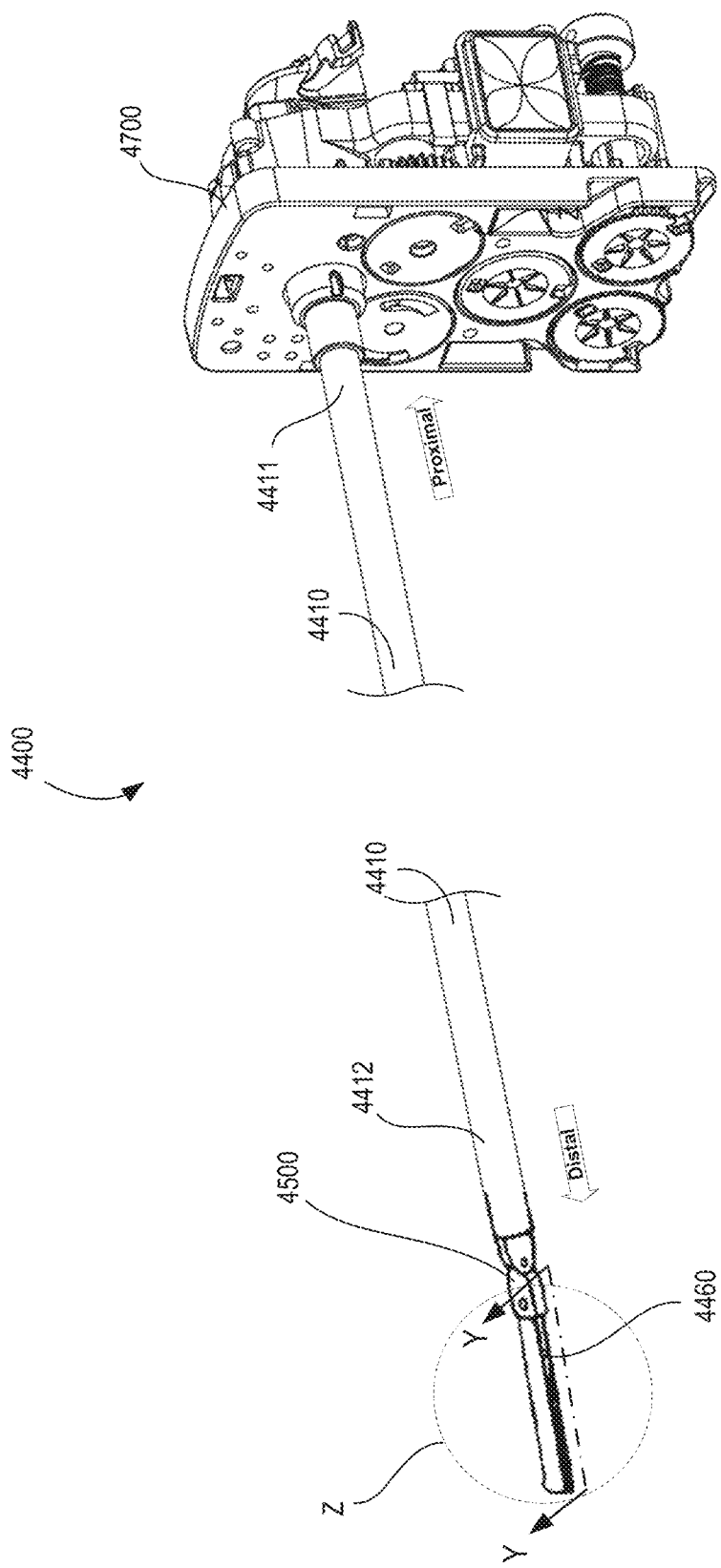
FIG. 8 is a perspective view of an instrument of a surgery system, according to an embodiment.

Referring to FIGS. 8-9, the wrist assembly 4500 of the instrument 4400 includes the end effector 4460, a proximal clevis 4510, and a distal clevis 4610. The proximal clevis 4510 has a proximal end portion coupled to the distal end portion 4412 of the shaft 4410. A distal end portion 4512 of the proximal clevis 4510 includes a joint portion that is rotatably coupled to a mating joint portion of the distal clevis 4610. Specifically, the proximal clevis 4510 is coupled to the distal clevis 4610 by a pin 4543. In this manner, the proximal clevis 4510 and the distal clevis 4610 form the wrist assembly 4500 having a first axis of rotation $A_1$ (also referred to as the pitch axis) about which the distal clevis 4610 can rotate relative to the proximal clevis 4510.

The distal clevis 4610 has a proximal end portion 4611 and a distal end portion 4612. As described above, the proximal end portion 4611 includes a joint portion that is rotatably coupled to the proximal clevis 4510. The distal end portion 4612 of the distal clevis 4610 includes a connector 4680 that is coupled to the end effector 4460. The connector 4680 includes the pin 4683 which is supported by (and placed within) the pin openings. In this manner, the retractor blades can rotate relative to the distal clevis 4610 about a second axis of rotation (also referred to as the yaw axis) $A_2$. In some embodiments, the connector 4680 can include any of the structure and features of the pinned joints shown and described in U.S. Pat. No. 9,204,923 B2 (filed Jul. 16, 2008), entitled "Medical Instrument Electronically Energized Using Drive Cables," which is incorporated herein by reference in its entirety. As shown in FIG. 9, the second axis of rotation $A_2$ (also referred to as the yaw axis) is non-parallel to the pitch axis $A_1$. Thus, the instrument 4400 provides for up to three degrees of freedom (i.e., a pitch motion about the first axis of rotation $A_1$, a yaw rotation about the second axis of rotation $A_2$, and a grip motion about the second axis of rotation $A_2$).

As shown in FIGS. 9-12, the end effector 4460 includes a first tool member 4462 (which functions as a first, or outer, retractor blade), a pair of second tool members 4482 (which function as the second, or intermediate, retractor blades), and a third tool member 4582 (which functions as a third, or outer, retractor blade). As described herein, during certain operations, the end effector 4460 is configured such that the first retractor blade 4462 can rotate relative to the clevis while the second retractor blades 4482 remains in a fixed position, while in other operations, rotation of the first retractor blade 4462 causes rotation of (i.e., drives) one or both of the second retractor blades 4482. Similarly, during certain operations, the third retractor blade 4582 can rotate relative to the clevis while the second retractor blades 4482 remains in a fixed position, while in other operations, rotation of the third retractor blade 4582 causes rotation of (i.e., drives) one or both of the second retractor blades 4482.

The first retractor blade 4462 has a proximal end portion 4467 and an opposite distal end portion 4463. The first retractor blade 4462 also has a first (outer) side 4464 (see FIG. 10) and a second (inner) side 4465 (see FIG. 11). The distal end portion 4463 includes a curved tip 4466, and the first retractor blade 4462 defines fenestrations 4478 that extend from the first side 4464 to the second side 4465. Thus, either the first side 4464 or the second side 4465 (or both) can function to engage target tissue when the instrument 4400 performs retractor functions. In addition to the fenestrations 4478, the first side 4464 or the second side 4465 can include any suitable features to facilitate interaction with tissue. The proximal end portion 4467 defines a guide channel 4470, a central opening 4468, and a tension member opening 4469. The guide channel 4470 receives a distal end portion of the first tension member 4420 and the tension member opening 4469 receives a swage 4424 of the first tension member 4420 (see FIG. 9) to couple the first tension member 4420 to the first retractor blade 4462. The proximal end portion 4467 is rotatably coupled to the distal clevis 4610 via the pin 4683, which is disposed within the central opening 4468. In this manner, when a torque is applied to the first retractor blade 4462 by the first tension member 4420, the first blade 4462 rotates about the pin 4683 and relative to the distal clevis 4610 about the second axis of rotation $A_2$. The proximal end portion 4467 also includes a first pin 4472 that couples the first retractor blade 4462 to the adjacent second retractor blade 4482. Specifically, the first pin 4472 extends from the second side 4465 of the first retractor blade 4462 and into a slot 4492 of the adjacent second retractor blade 4482. The first pin 4472 interacts with the slot 4492, as described herein, to produce the desired rotational movement of the second retractor blade 4482.

As shown in FIGS. 10-12, 15, and 16, each of the two second retractor blades 4482 has a proximal end portion 4487 and an opposite distal end portion 4483. Each second retractor blade 4482 also has a first (outer) side 4484 (see FIG. 10) and a second (inner) side 4485 (see FIG. 11). The distal end portion 4483 includes a curved tip 4486, and each second retractor blade 4482 defines fenestrations 4498 that extend from the first side 4484 to the second side 4485. Thus, either the first side 4484 or the second side 4485 (or both) can function to engage target tissue when the instrument 4400 performs retractor functions. In addition to the fenestrations 4498, the first side 4484 or the second side 4485 can include any suitable features to facilitate interaction with tissue. The proximal end portion 4487 is rotatably coupled to the distal clevis 4610 via the pin 4683, which is disposed within the central opening 4488. In this manner, when a torque is applied to the second retractor blade 4482 (by either the first retractor blade 4462, an adjacent second retractor blade 4482, or the third retractor blade 4582), the second blade 4482 rotates about the pin 4683 and relative to the distal clevis 4610 about the second axis of rotation $A_2$. The proximal end portion 4487 also includes a second pin 4493 and defines the slot 4492. As described above, the slot 4492 functions to couple one of the second blades 4482 to the first retractor blade 4462 (via the first pin 4472) and the other second blade 4482 to the adjacent second blade 4482 (via the second pin 4492 of the adjacent second blade). Specifically, the first pin 4472 (of the first blade 4462) extends into the slot 4492 of the second retractor blade 4482. The second pin 4493 (of the second blade 4482 that is coupled to the first blade 4462) extends from the second side 4485 and into the slot 4492 of the second blade 4482 that is adjacent the third blade 4582.

The third retractor blade 4582 has a proximal end portion 4587 and an opposite distal end portion 4583. The third retractor blade 4582 also has a first (outer) side 4584 (see FIG. 10) and a second (inner) side 4585 (see FIG. 11). The distal end portion 4583 includes a curved tip 4586, and the third retractor blade 4582 defines fenestrations 4598 that extend from the first side 4584 to the second side 4585. Thus, either the first side 4584 or the second side 4585 (or both) can function to engage target tissue when the instrument 4400 performs retractor functions. In addition to the fenestrations 4598, the first side 4584 or the second side 4585 can include any suitable features to facilitate interaction with tissue. The proximal end portion 4587 defines a guide channel 4590, a central opening 4588, and a tension member opening 4589. The guide channel 4590 receives a distal end portion of the second tension member 4430 and the tension member opening 4589 receives a swage 4434 of the second tension member 4430 (see FIG. 9) to couple the second tension member 4430 to the third retractor blade 4582. The proximal end portion 4587 is rotatably coupled to the distal clevis 4610 via the pin 4683, which is disposed within the central opening 4588. In this manner, when a torque is applied to the third retractor blade 4582 by the second tension member 4430, the third blade 4482 rotates about the pin 4683 and relative to the distal clevis 4610 about the second axis of rotation $A_2$. The proximal end portion 4587 also defines a slot 4592 that functions to couple the third retractor blade 4582 to the adjacent second retractor blade 4482. Specifically, the second pin 4493 extending from the adjacent second retractor blade 4482 is within the slot 4592 of the third retractor blade 4582. The second pin 4493 interacts with the slot 4592, as described herein, to produce the desired rotational movement of the second retractor blade 4482 that is coupled directly to the third retractor blade 4582.

Although the specific blades are shown as having specific coupling features (i.e., the first blade 4462 is shown as include a first pin 4472 that couples the first blade 4462 to a slot 4492 of the second blade 4482), in other embodiments, the first blade 4462, the second blade 4482, or any other blades described herein can include any coupling portion or mechanism as described herein (including any pins, slots, springs, or the like).

Similar to the operation of the instrument 2400, in use, the end effector 4460 can be moved between a closed configuration and many different opened configurations. When the end effector 4460 is in the closed configuration, the first retractor blade 4462 is aligned with the third retractor blade 4582 and the second retractor blades 4482. In the closed configuration, the offset angle between the first retractor blade 4462, the third retractor blade 4582 and the second retractor blades 4482 is zero. When the instrument 4400 is in the closed configuration, the end effector 4460 can be advanced through a cannula (not shown) towards a surgical environment. The instrument 4400 can then be actuated (e.g., by applying a tension on the first tension member 4420, the second tension member 4430, or both to move the instrument 4400 to one or more opened configurations for tissue retraction or other operations.

As described above, the first retractor blade 4462 is directly driven by the first tension member 4420 and the third retractor blade 4582 is directly driven by the second tension member 4430. Said another way, the first tension member 4420 is directly coupled to the first retractor blade 4462 such that movement of (or torque exerted by) the first tension member 4420 produces movement of the first retractor blade 4462. The second tension member 4430 is directly coupled to the third retractor blade 4582 such that movement of (or torque exerted by) the second tension member 4420 produces movement of the third retractor blade 4582. The second retractor blades 4482 are coupled between (and to) the first retractor blade 4462 and the third retractor blade 4582 such that they are indirectly moved by the tension members 4420, 4430. Similarly stated, the second retractor blades 4482 are driven solely by the rotation of the first retractor blade 4462 or the third retractor blade 4582. This arrangement allows the end effector 4460 having more than two blades to be moved between various configurations by two tension members.

Like the arrangement described above for the instrument 2400, the retractor blades are coupled by the pins and slots such that the second retractor blades 4482 can remain in a fixed position relative to the clevis 4610 when the adjacent first retractor blade 4462 or third retractor blade 4582 is moved. Specifically, the first pin 4472 and the second pins 4493 can move along a rotation path when the retractor blades rotate relative to the clevis 4610. The slots 4492 and 4592 can be curved in a manner that is aligned with at least a portion of the rotation path of the pins. In this manner, the first pin 4472 can move within the slot 4492 during a portion of the rotation of the first retractor blade 4462. This allows the first retractor blade 4462 to rotate independently from the second retractor blade 4482, and vice-versa. When the rotation path is no longer aligned with the curved portion of the slot 4492, however, the first pin 4472 engages a portion of the second retractor blade 4482 (e.g., a s side wall) and drives the second retractor blade. Similarly, the pins 4493 can move within the slot 4492 (and the slot 4592 of the third retractor blade). This allows the mating retractor blades to rotate independently from each other. When the rotation path is no longer aligned with the curved portion of the slot 4492, however, the pins 4493 engage a portion of the adjacent retractor blade (e.g., a s side wall) and drive the adjacent retractor blade, or otherwise allows the adjacent retractor blade (i.e., the third retractor blade 4582) to drive the adjacent blade.

Figure 17:
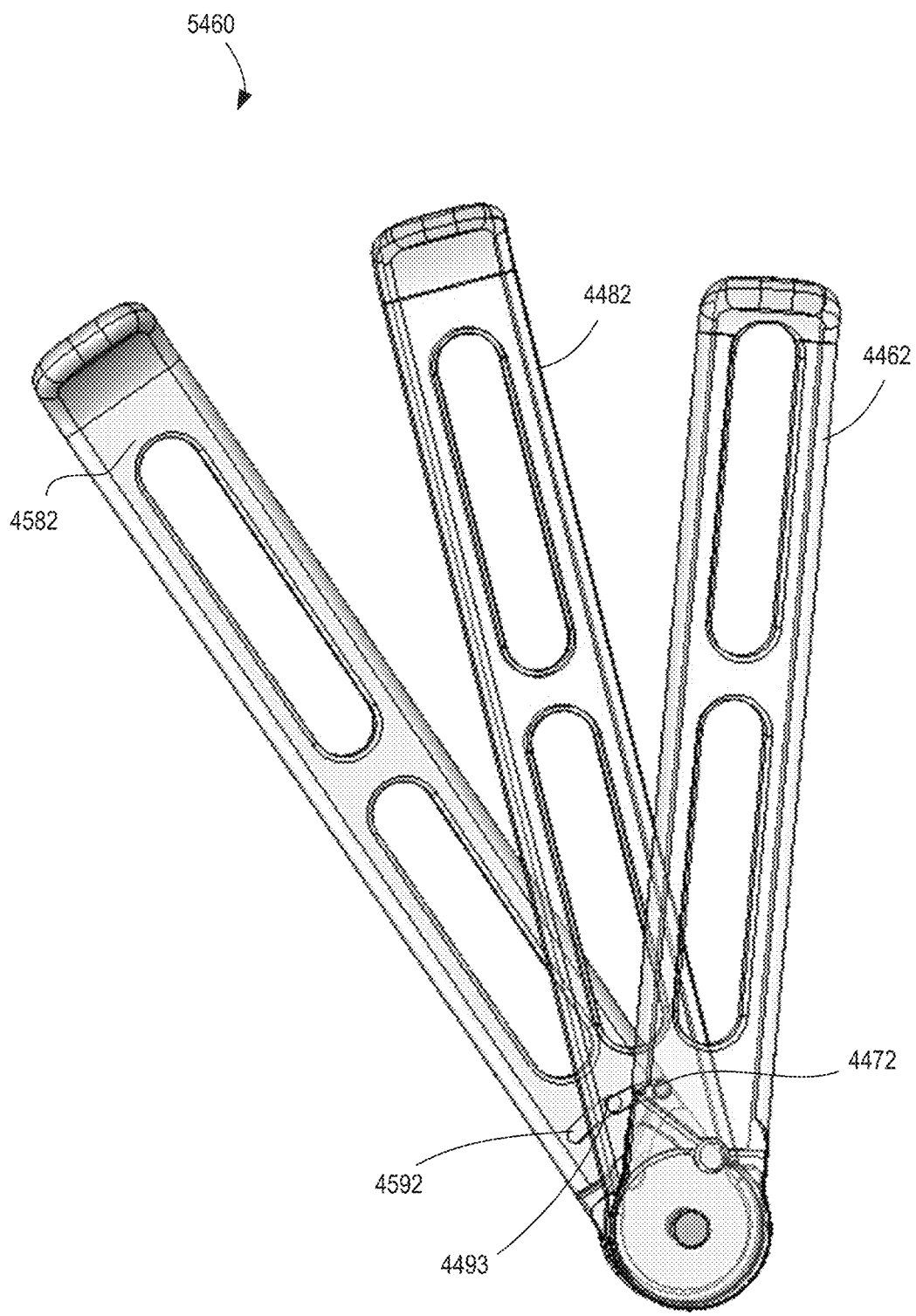
FIG. 17 is a perspective view of a set of the retractor blades according to an embodiment, which can be used in the instrument shown in FIGS. 8 and 9.

Although the instrument 4400 is shown and described as including four retractor blades, in other embodiments, a retractor instrument can include any suitable number of retractor blades. For example, in some embodiments, an instrument can include three, five, or more retractor blades, with two of the retractor blades being drive blades that are on the outside (or end) of the remaining blades. For example, FIG. 17 shows an end effector 5460 according to an embodiment that includes three retractor blades. As shown, the end effector 5460 includes a first retractor blade 4462, a third retractor blade 4582, and a second retractor blade 4482 coupled between (and driven by) the first retractor blade 4462 and the third retractor blade 4582. The retractor blades of the end effector 5460 are the same as those described above for the end effector 4460 and are therefore not described in detail.

Although the slots 4492 and 4592 are shown as being curved in a manner that is aligned with a rotation path of one of the first pin 4472 or the second pins 4493, in other embodiments, a retractor blade can include coupling portion (or slot) having any suitable shape. Similarly stated, although the slots 4492 and 4592 are shown as being shaped and sized to allow the second retractor blades 4482 to rotate independently from the first retractor blade 4462 or the third retractor blade 4582, in other embodiments and end effector can be configured to allow a portion of torque from one of the drive blades to be transferred to one of the driven blades throughout the range of rotation. Such an arrangement can, for example, result in a self-centering set of blades (i.e., an end effector in which the intermediate blades are centered between the outer, drive blades). For example, FIGS. 18-21 show a portion of an instrument 6400, according to an embodiment. The instrument 6400 is similar in many respects to the instrument 5400, and therefore portions of the instrument 6400 (e.g., the transmission, the shaft, and the tension members) are not shown or described in detail. For example, although not shown in FIGS. 18-21, the instrument 6400 includes at least two tension members (similar to the first tension member 4420 and the second tension member 4430) that couple a transmission (not shown) to the outer retractor blades of the end effector 6460.

Figure 18:
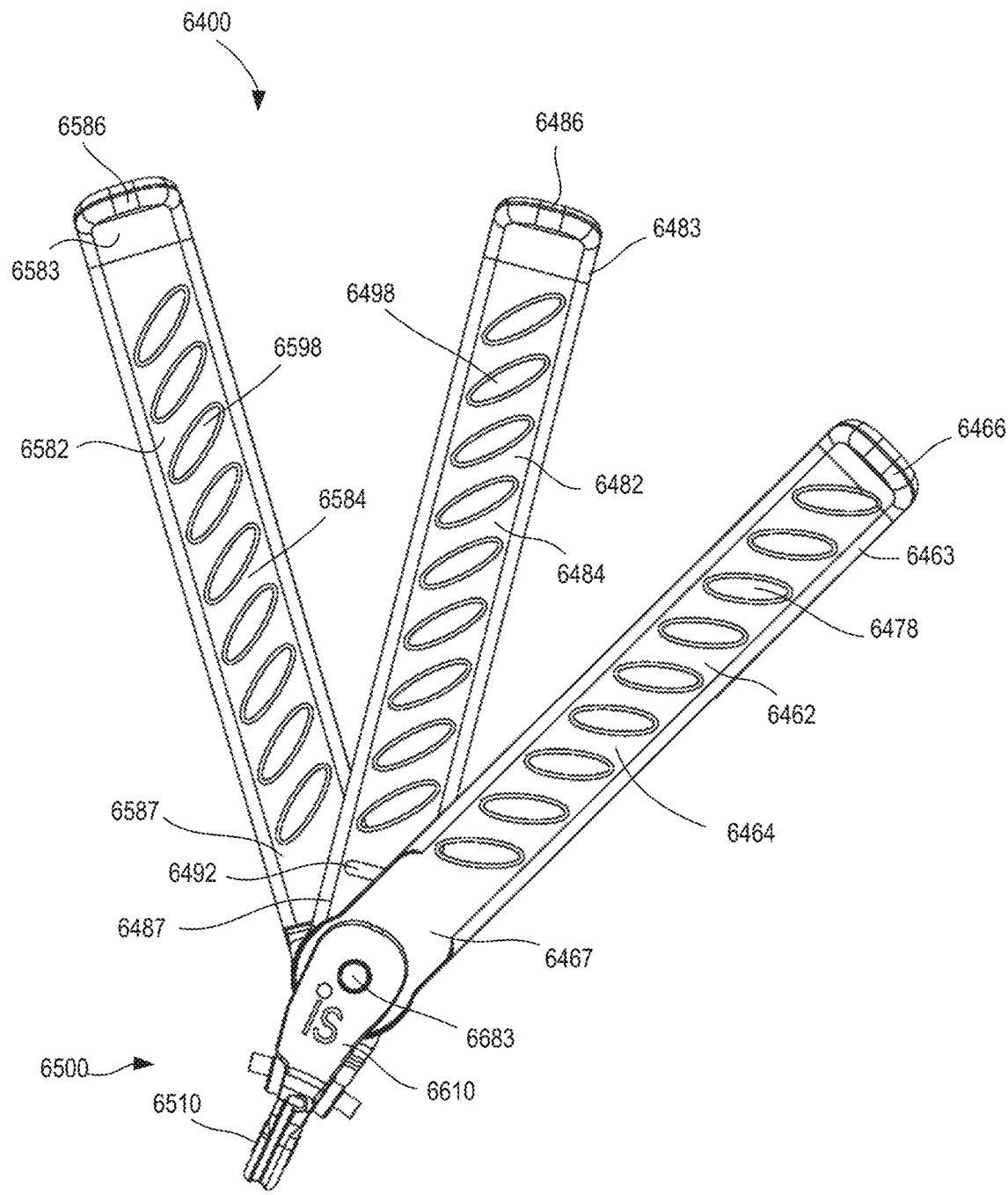
FIG. 18 is a perspective view of a wrist assembly including set of the retractor blades according to an embodiment, which can be used in the instrument shown in FIGS. 8 and 9.

Referring to FIG. 18, the wrist assembly 6500 of the instrument 6400 includes the end effector 6460, a proximal clevis 6510, and a distal clevis 6610. The proximal clevis 6510 has a proximal end portion coupled to a shaft (not shown). A distal end portion of the proximal clevis 6510 includes a joint portion that is rotatably coupled to a mating joint portion of the distal clevis 6610. In this manner, the proximal clevis 6510 and the distal clevis 6610 form the wrist assembly 6500 having a first axis of rotation (also referred to as the pitch axis) about which the distal clevis 6610 can rotate relative to the proximal clevis 6510. The distal clevis 6610 includes a connector, which includes a pin 6683, that is coupled to the end effector 6460. In this manner, the retractor blades can rotate relative to the distal clevis 6610 about a second axis of rotation (also referred to as the yaw axis).

The end effector 6460 includes a first tool member 6462 (which functions as a first, or outer, retractor blade), a second tool member 6482 (which functions as the second, or intermediate, retractor blade), and a third tool member 6582 (which functions as a third, or outer, retractor blade). As described herein, during certain operations, the end effector 6460 is configured such that the first retractor blade 6462 can rotate relative to the clevis 6610 via a torque applied by a tension member while second retractor blade 6482 is moved by and remains centered between the first retractor blade 6462 and the third retractor blade 6582.

The first retractor blade 6462 has a proximal end portion 6467 and an opposite distal end portion 6463. The first retractor blade 6462 also has a first (outer) side 6464 (see FIG. 19) and a second (inner) side 6465 (see FIG. 20). The distal end portion 6463 includes a curved tip 6466, and the first retractor blade 6462 defines fenestrations 6478 that extend from the first side 6464 to the second side 6465. Thus, either the first side 6464 or the second side 6465 (or both) can function to engage target tissue when the instrument 6400 performs retractor functions. As shown in FIG. 20, the proximal end portion 6467 defines a guide channel 6470, a central opening 6468, and a tension member opening 6469. The guide channel 6470 receives a distal end portion of the first tension member (not shown) and the tension member opening 6469 receives a swage or other coupling member of the first tension member to couple the first tension member to the first retractor blade 6462. The proximal end portion 6467 is rotatably coupled to the distal clevis 6610 via the pin 6683, which is disposed within the central opening 6468. In this manner, when a torque is applied to the first retractor blade 6462 by the first tension member, the first blade 6462 rotates about the pin 6683 and relative to the distal clevis 6610. The proximal end portion 6467 also includes a first pin 6472 that couples the first retractor blade 6462 to the second retractor blade 6482. Specifically, the first pin 6472 extends from the second side 6465 of the first retractor blade 6462 and into a slot (or portion of a slot) 6492 of the second retractor blade 6482. The first pin 6472 interacts with the slot 6492, as described herein, to maintain the second retractor blade 6482 centered between the first retractor blade 6462 and the third retractor blade 6582.

Figure 19:
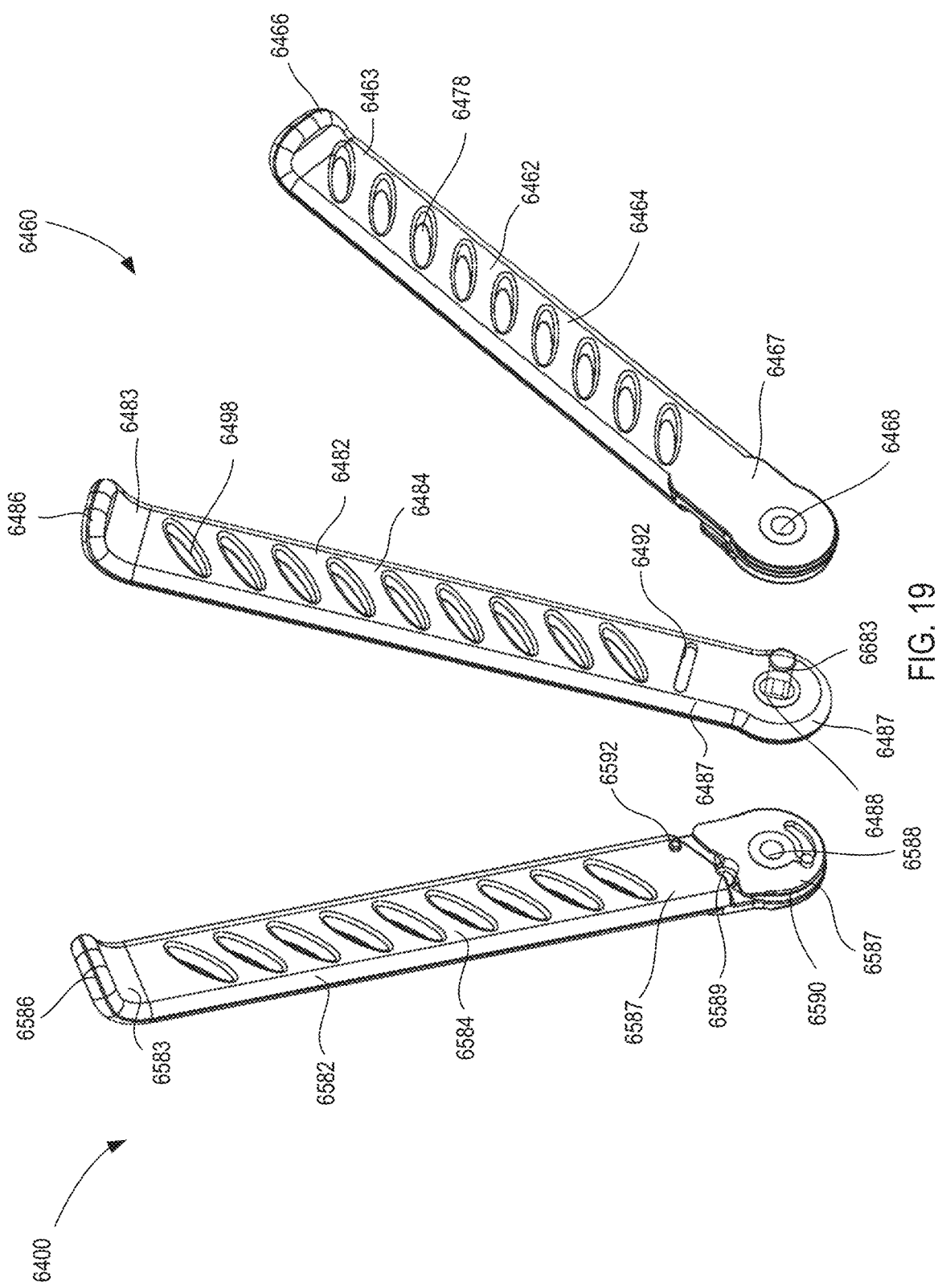
FIGS. 19 and 20 are perspective views of the retractor blades shown in FIG. 18, showing a first side of the retractor blades (FIG. 19) and a second side of the retractor blades (FIG. 20).
Figure 20:
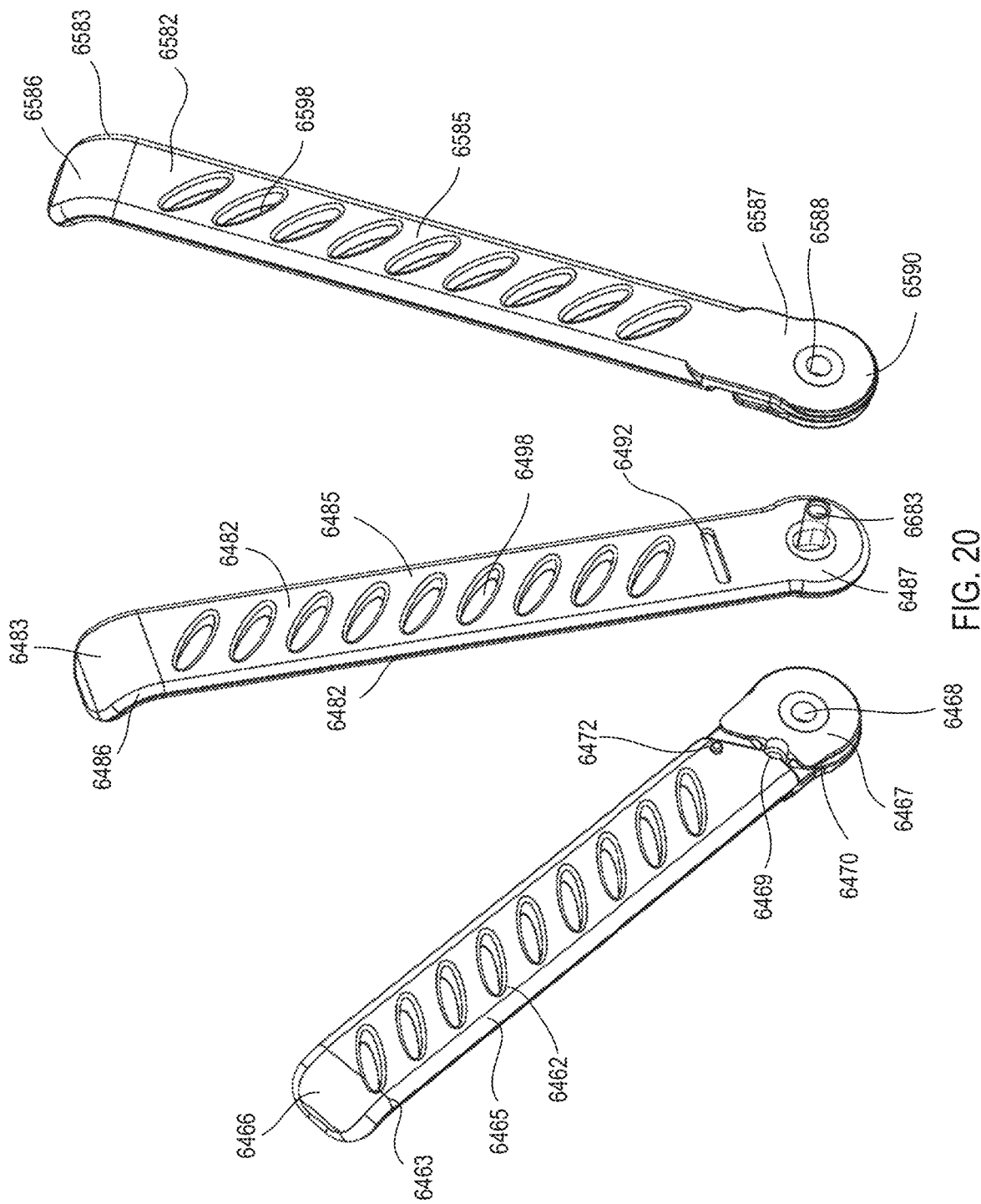

As shown in FIGS. 19-20, the second retractor blade 6482 has a proximal end portion 6487 and an opposite distal end portion 6483. The retractor blade 6482 also has a first (outer) side 6484 (see FIG. 19) and a second (inner) side 6485 (see FIG. 20). The distal end portion 6483 includes a curved tip 6486, and the second retractor blade 6482 defines fenestrations 6498 that extend from the first side 6484 to the second side 6485. Thus, either the first side 6484 or the second side 6485 (or both) can function to engage target tissue when the instrument 6400 performs retractor functions. The proximal end portion 6487 is rotatably coupled to the distal clevis 6610 via the pin 6683, which is disposed within the central opening 6488. In this manner, when a torque is applied to the second retractor blade 6482 (by either or both of the first retractor blade 6462 and the third retractor blade 6582), the second blade 6482 rotates about the pin 6683 and relative to the distal clevis 6610. The proximal end portion 6487 also defines the slot 6492. The slot 6492 extends through the second blade 6482 and couples the second blade 6482 to the first retractor blade 6462 (via the first pin 6472) and the third blade 6582 (via the second pin 6592). Specifically, the first pin 6472 (of the first blade 6462) extends into the slot 6492 of the second retractor blade 6482 from the first side 6484. The second pin 6592 (of the third blade 6582) extends into the slot 6492 from the second side 6485. The slot 6592 is a linear slot that is substantially perpendicular to a longitudinal center line $CL_2$ of the second blade 6482 (see FIG. 21). Although described as being a "through slot," in other embodiments, the second blade 6482 can include first slot that extends only partially through the blade and receives the first pin, and a second slot that also extends only partially through the blade and receives the second pin.

The third retractor blade 6582 has a proximal end portion 6587 and an opposite distal end portion 6583. The third retractor blade 6582 also has a first (outer) side 6584 (see FIG. 19) and a second (inner) side 6585 (see FIG. 20). The distal end portion 6583 includes a curved tip 6586, and the third retractor blade 6582 defines fenestrations 6598 that extend from the first side 6584 to the second side 6585. Thus, either the first side 6584 or the second side 6585 (or both) can function to engage target tissue when the instrument 6400 performs retractor functions. The proximal end portion 6587 defines a guide channel 6590, a central opening 6588, and a tension member opening 6589. The guide channel 6590 receives a distal end portion of the second tension member (not shown) and the tension member opening 6589 receives a swage or coupling portion of the second tension member to couple the second tension member to the third retractor blade 6582. The proximal end portion 6587 is rotatably coupled to the distal clevis 6610 via the pin 6683, which is disposed within the central opening 6588. In this manner, when a torque is applied to the third retractor blade 6582 by the second tension member, the third blade 6482 rotates about the pin 6683 and relative to the distal clevis 6610. The proximal end portion 6587 also includes the second pin 6592 that functions to couple the third retractor blade 6582 to the second retractor blade 6482. Specifically, the second pin 6492 extends into the slot 6492, as described above.

Although the specific blades are shown as having specific coupling features (i.e., the first blade 6462 is shown as include a first pin 6472 that couples the first blade 6462 to a slot 6492 of the second blade 6482), in other embodiments, the first blade 6462, the second blade 6482, and the third blade 6582 can include any coupling portion or mechanism as described herein (including any pins, slots, springs, or the like).

Similar to the operation of the instrument 3400, in use, the end effector 6460 can be moved between a closed configuration and many different opened configurations. When the end effector 6460 is in the closed configuration, the first retractor blade 6462, the second retractor blade 6482, and the third retractor blade 6582 are aligned. In the closed configuration, the offset angle α between the center line $CL_1$ of the first retractor blade 6462 and the center line $CL_2$ of the second retractor blade 6482 is zero. Likewise, the offset angle β between the center line $CL_3$ of the third retractor blade 6582 and the center line $CL_2$ of the second retractor blade 6482 is zero. When the instrument 6400 is in the closed configuration, the end effector 6460 can be advanced through a cannula (not shown) towards a surgical environment. The instrument 6400 can then be actuated (e.g., by applying a tension on the first tension member, the second tension member, or both to move the instrument 6400 to one or more opened configurations for tissue retraction or other operations.

The first retractor blade 6462 is directly driven by the first tension member and the third retractor blade 6582 is directly driven by the second tension member. The second retractor blade 4482 is coupled between (and to) the first retractor blade 4462 and the third retractor blade 4582 such that it is indirectly moved by the tension members. Similarly stated, the second retractor blade 4482 is driven solely by the rotation of the first retractor blade 4462 or the third retractor blade 4582. This arrangement allows the end effector 4460 having more than two blades to be moved between various configurations by two tension members.

Figure 21:
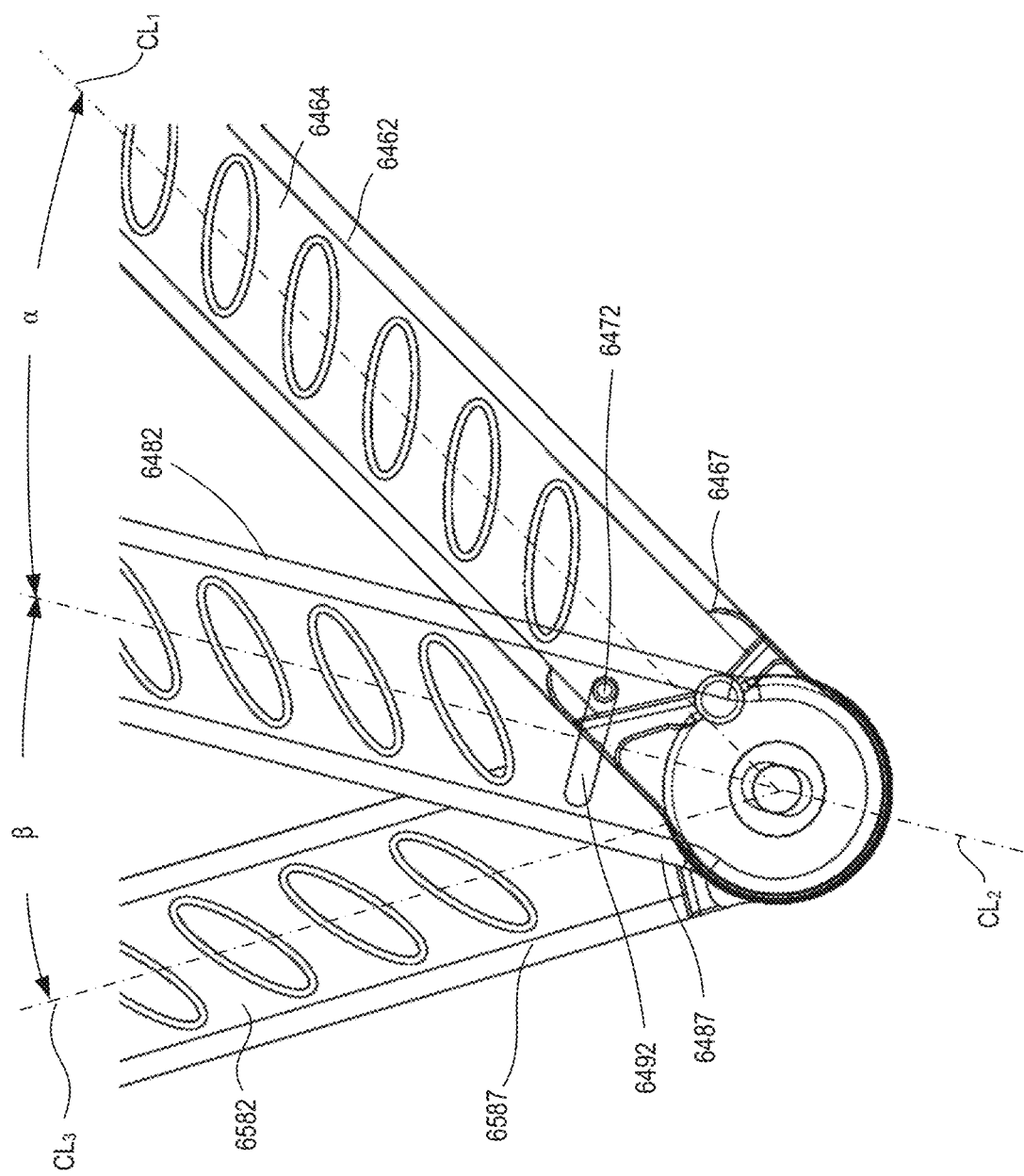
FIG. 21 is a front view of proximal end portion of the retractor blades shown in FIG. 18.
Figure 22:
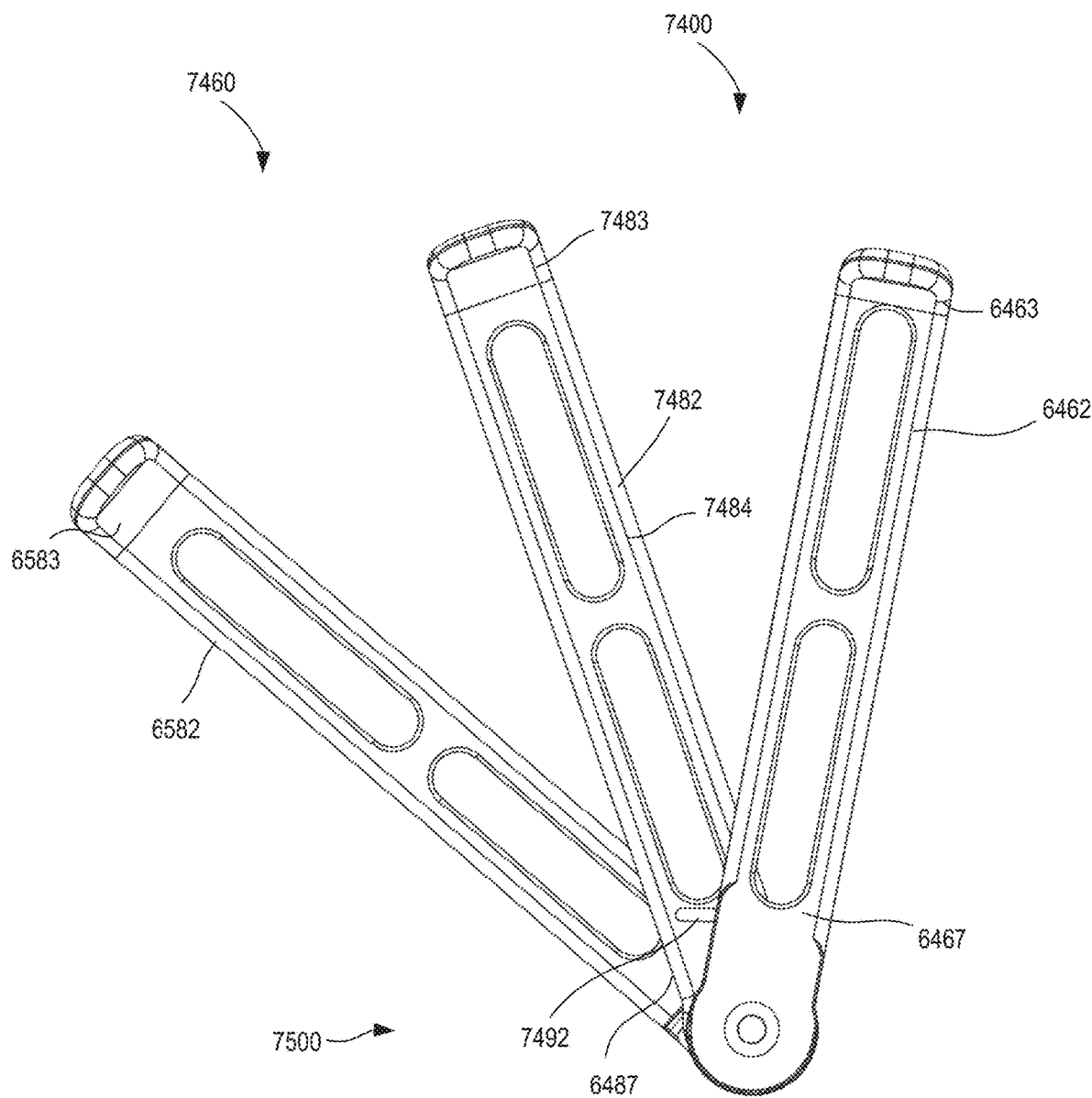
FIGS. 22 and 23 are a front view (FIG. 22) and a perspective view (FIG. 23) of a set of the retractor blades according to an embodiment, which can be used in the instrument shown in FIGS. 8 and 9.
Figure 23:
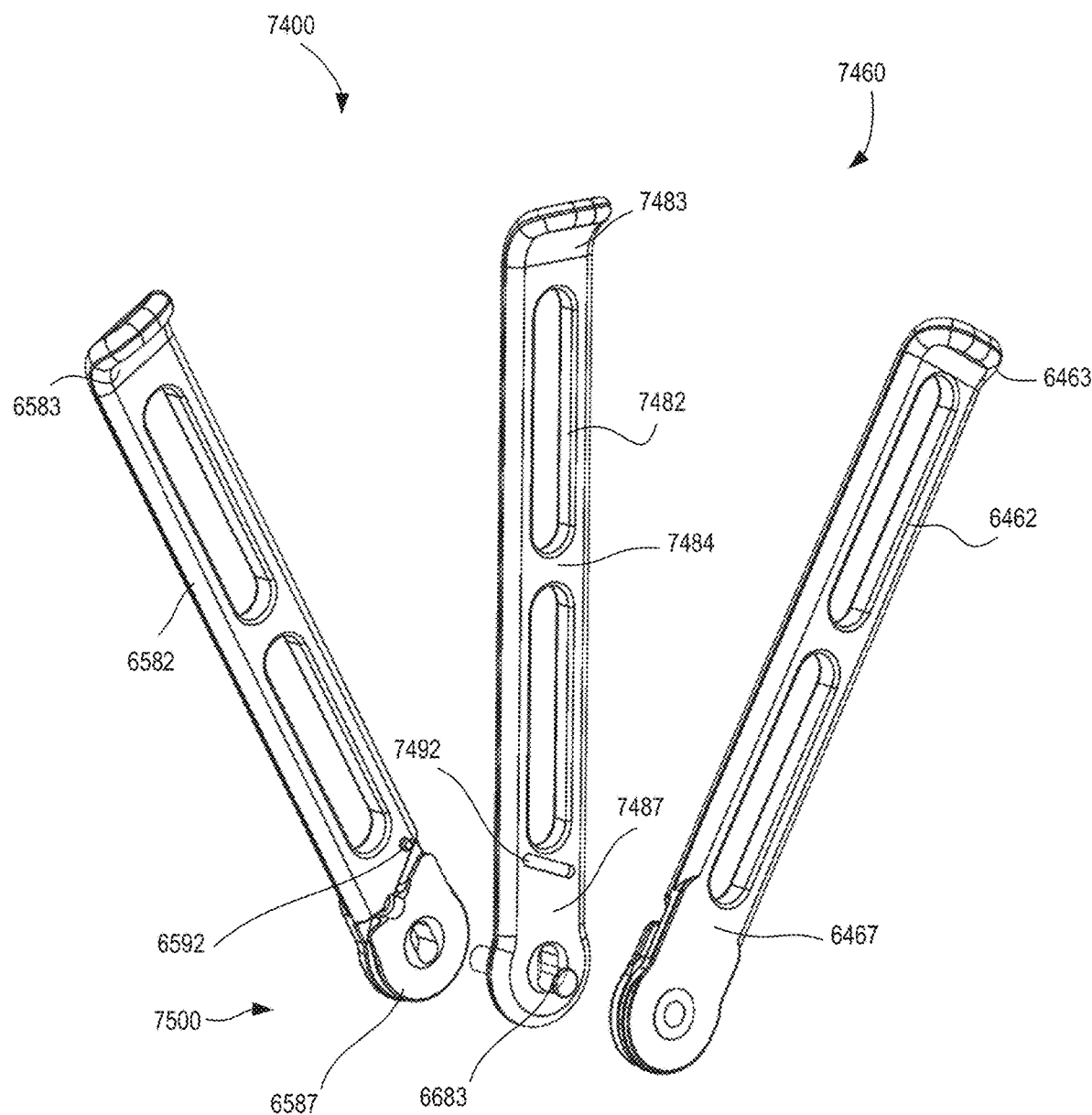
Figure 25:
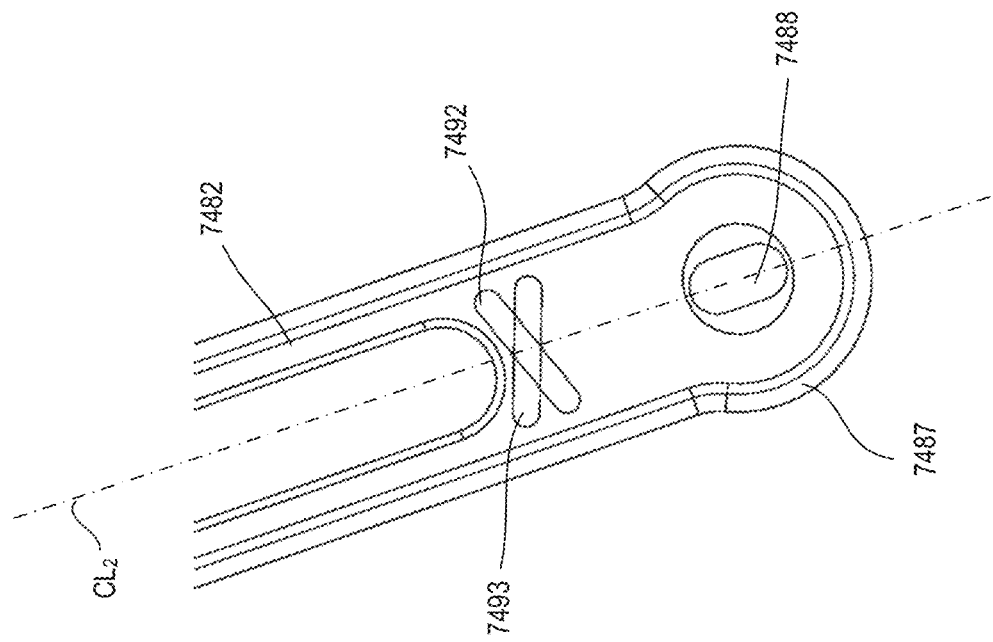
FIGS. 24 and 25 are front views of a proximal end portion of a second retractor blade of the set of blades shown in FIGS. 22 and 23, showing a first side (FIG. 24) and a transparent view showing both the first side and portions of the second side (FIG. 25).
Figure 24:
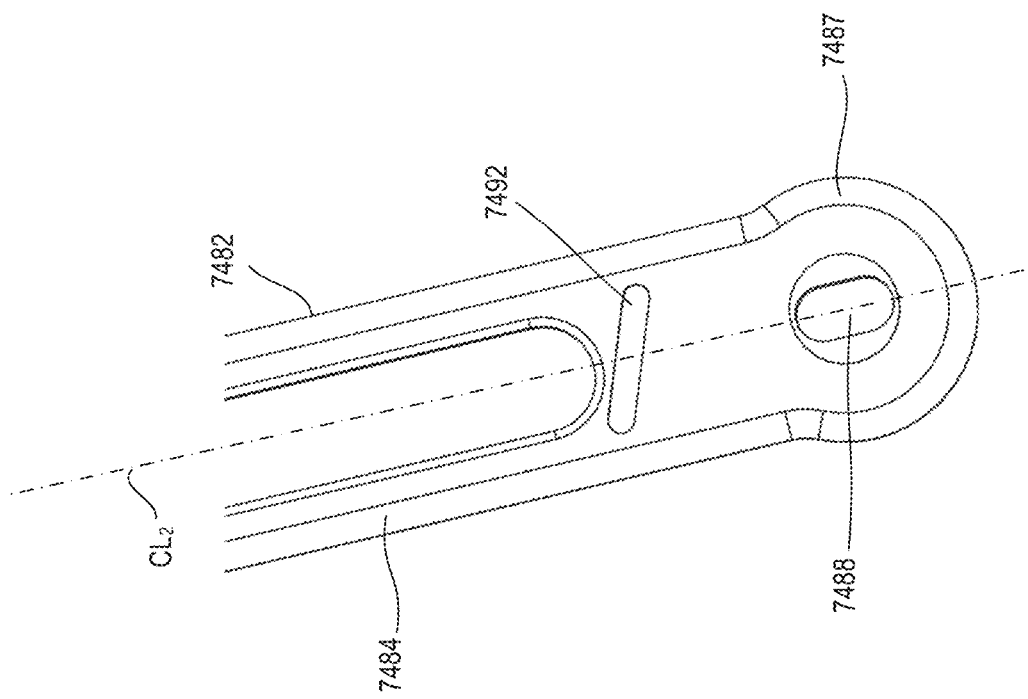

Moreover, like the arrangement described above for the instrument 3400, the retractor blades are coupled by the first pin 6472, the second pin 6592 and the slot 6492 such that the second retractor blade 6482 remains centered between the first retractor blade 6462 and the third retractor blade 6562. Similarly stated, the pins and the slot are configured such that when the first retractor blade 6462 is in a first angular orientation and the third retractor blade 6562 is in a third angular orientation, the second retractor blade 6482 is in a second angular orientation that is centered between the first angular orientation and the third angular orientation. Referring to FIG. 21, when the end effector is in an opened configuration, the first center line $CL_1$ is offset from the second center line $CL_2$ by an offset angle α and the third center line $CL_3$ is offset from the second center line $CL_2$ by an offset angle β. The connection portions are configured such that the offset angle α is substantially equal to the offset angle β.

In some embodiments, the first pin 6472, the second pin 6592, and the slot 6492 can be configured such that the relative motion between these mating portions is balanced to produce substantially equal transfer of torque from the first blade 6462 and the third blade 6582 to the second retractor blade 6482. For example, in some embodiments, the first pin 6472 can move along a first rotation path and the second pin 6592 can move along a second rotation path (which can, in some instances, be aligned with the first rotation path). The slot 6492 can be within the first rotation path and the second rotation path such that the engagement between the coupling portions produces substantially equal torque transfer to the second retractor blade 6482. In some embodiments, the second coupling portion 6492 and the fourth coupling portion 6493 can be a slot that is at least partially aligned with rotation paths of the first coupling portion 6472 and the third coupling portion 6572. In some embodiments, the opening 6488 of the second blade 6482 can be elongated (e.g., along the second center line $CL_2$) to allow the second blade 6482 to translate relative to the pin 6683 during rotation. In this manner, the location of the slot 6492 relative to the rotation paths of the first pin 6472 and the second pin 6592 can be moved.

Although the slot 6492 is shown and described as being substantially normal to the second center line $CL_2$, in other embodiments a retractor blade can define one or more slots that is at an angle (i.e., an acute angle) to the blade center line. Changing the angle of the connection slot can change the force balance and intersection of the rotation path of a mating pin within the slot. Moreover, in some embodiments, an intermediate blade can include two different slots having different angle—one that engages one outer blade and another that engages the other outer blade. For example, FIGS. 22-25 show a portion of an instrument 7400, according to an embodiment. The instrument 7400 is similar in many respects to the instrument 6400 and 4400, and therefore portions of the instrument 7400 (e.g., the transmission, the shaft, and the tension members) are not shown or described in detail. For example, although not shown in FIGS. 18-21, the instrument 7400 includes at least two tension members (similar to the first tension member 4420 and the second tension member 4430) that couple a transmission (not shown) to the outer retractor blades of the end effector 7460.

Referring to FIG. 18, the wrist assembly 7500 of the instrument 7400 includes the end effector 7460, a proximal clevis (not shown), and a distal clevis (not shown). The end effector 7460 includes a first tool member 6462 (which functions as a first, or outer, retractor blade), a second tool member 7482 (which functions as the second, or intermediate, retractor blade), and a third tool member 6582 (which functions as a third, or outer, retractor blade). The first tool member 6462 is the same as the first tool member 6462 described above, and the third tool member 6582 is the same as the third tool member 6582 described above. As described herein, during certain operations, the end effector 7460 is configured such that the first retractor blade 6462 can rotate relative to the clevis 7610 via a torque applied by a tension member while second retractor blade 7482 is moved by and remains centered between the first retractor blade 6462 and the third retractor blade 6582.

The end effector 7460 differs from the end effector 6460 in that the second retractor blade 7482 includes a different slot configuration than that shown for the second retractor blade 6482. Specifically, the second retractor blade 7482 has a proximal end portion 7487 and an opposite distal end portion 7483. The retractor blade 7482 also has a first (outer) side 7484 (see FIGS. 22 and 23) and a second (inner) side. The proximal end portion 7487 is rotatably coupled to the distal clevis via the pin 6683, which is disposed within the central opening 7488. In this manner, when a torque is applied to the second retractor blade 7482 (by either or both of the first retractor blade 6462 and the third retractor blade 6582), the second blade 7482 rotates about the pin 7683. The proximal end portion 7487 also defines a first slot 7492 and a second slot 7493 (see FIG. 25). The first slot 7492 is defined by the first side 7484 and extends only partially through the second blade 7482. The first slot 7492 is not normal to the center line $CL_2$ of the second retractor blade 7482. Said another way, the first slot 7492 is angled (i.e., forms an acute angle) with the center line $CL_2$. The first slot 7492 couples the second blade 7482 to the first retractor blade 6462 (via the first pin 6472). Specifically, the first pin 6472 (of the first blade 6462) extends into the first slot 7492 from the first side 7484.

The second slot 7493 is defined by the second side and extends only partially through the second blade 7482. The second slot 7493 is not normal to the center line $CL_2$ of the second retractor blade 7482. Said another way, the second slot 7493 is angled (i.e., forms an acute angle) with the center line $CL_2$. The second slot 7493 couples the second blade 7482 to the third retractor blade 6582 (via the second pin 6592). Specifically, the second pin 6592 (of the third blade 6582) extends into the second slot 7493 from the first side. Although the second slot 7493 is shown as being at an angle that is equal in magnitude but opposite in direction from the first slot 7492, in other embodiments, the first slot 7492 and the second slot 7493 can be at any suitable angle.

Similar to the operation of the instrument 3400 and instrument 6400, in use, the end effector 7460 can be moved between a closed configuration and many different opened configurations. When the end effector 7460 is in the closed configuration, the first retractor blade 6462, the second retractor blade 7482, and the third retractor blade 6582 are aligned. The pins and the slots described are configured such that the second retractor blade 7482 remains centered between the first retractor blade 7462 and the third retractor blade 7562. Similarly stated, the pins and the slot are configured such that when the first retractor blade 7462 is in a first angular orientation and the third retractor blade 7562 is in a third angular orientation, the second retractor blade 7482 is in a second angular orientation that is centered between the first angular orientation and the third angular orientation.

Figure 26C:
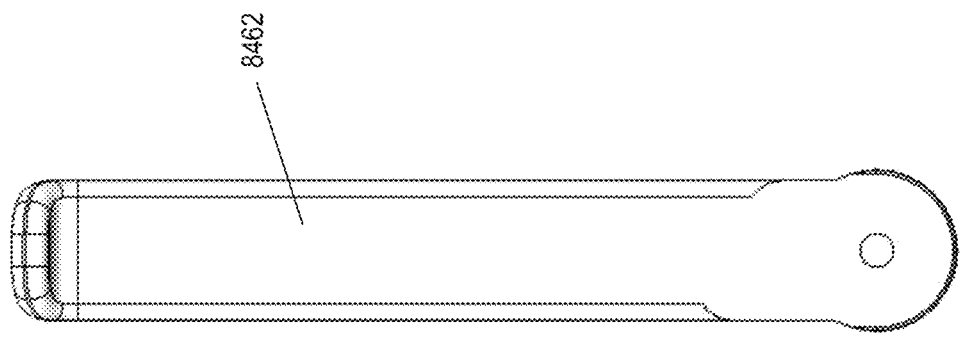
FIG. 26C is a front view of a retractor blade according to an embodiment, showing a non-fenestrated blade.
Figure 26B:
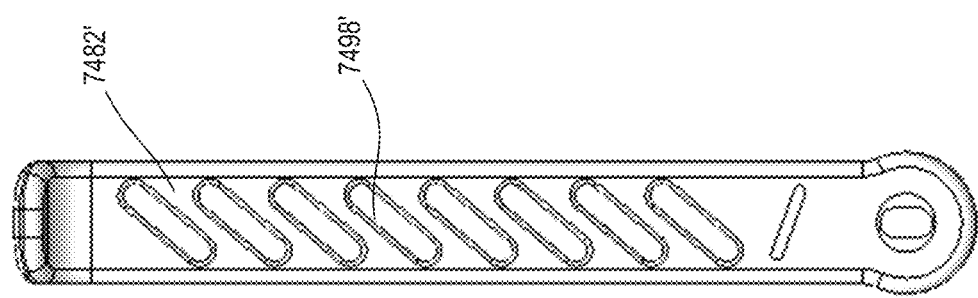
FIG. 26B is a front view of a retractor blade according to an embodiment, showing a rectangular fenestration pattern.
Figure 26A:
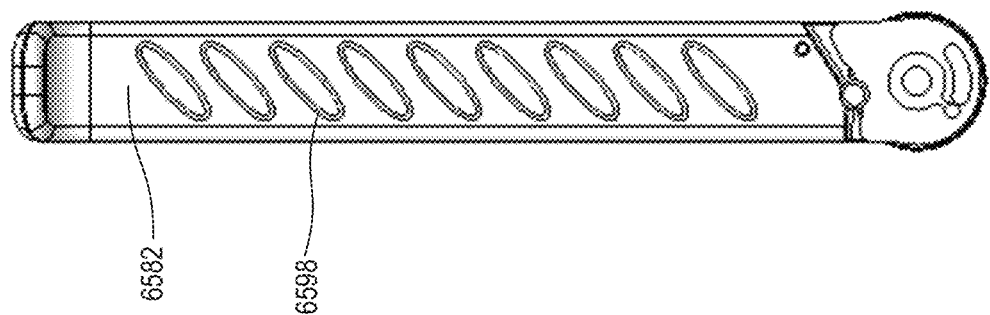
FIG. 26A is a front view of a retractor blade of the wrist assembly shown in in FIG. 18, showing the fenestration patterns.

Any of the retractor blades described herein can have any suitable fenestration or other features to improve operation (e.g., tissue purchase). For example, FIG. 26A shows the retractor blade 6582 described herein, which has a set of oval-shaped fenestrations 6598. FIG. 26B shows a retractor blade 7482', which is similar to the retractor blade 7482, but instead has a set of substantially rectangular fenestrations 7498'. FIG. 26C shows a retractor blade 8462, which can be similar to any of the retractor blades described herein, but that does not include any fenestrations.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the first tool member 2462, the second tool member 2482, and the third tool member 2562 (or any of the retractor blades described herein) can be moved by a miniature motor, a hydraulic actuator, or the like.

For example, any of the instruments described herein (and the components therein) are optionally parts of a surgical assembly that performs minimally invasive surgical procedures, and which can include a patient-side cart, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

Any of the tool members can be constructed from any material, such as medical grade stainless steel, nickel alloys, titanium alloys, or the like. Further, any of the devises, retractor blades, tension members, or components described herein can be constructed from multiple pieces that are later joined together. For example, in some embodiments, a retractor blade can be constructed by joining together separately constructed components. In other embodiments, however, any of the components described herein can be monolithically constructed.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. An apparatus comprising:
   a clevis defining an axis of rotation;
   a first retractor blade being rotatably coupled to the clevis;
   a second retractor blade being rotatably coupled to the clevis;
   a third retractor blade being rotatably coupled to the clevis, the third retractor blade being between the first retractor blade and the second retractor blade;
   a first coupling feature being between the first retractor blade and the third retractor blade, the first coupling feature comprising a first drive pin engaged with a first slot; and
   a second coupling feature being between the second retractor blade and the third retractor blade, the second coupling feature comprising a second drive pin received within a second slot.

2. The apparatus of claim 1, further comprising:
   a clevis connector extending between ears of the clevis; and
   an elongated opening defined in the third retractor blade, the clevis connector extending through the elongated opening.

3. The apparatus of claim 1, further comprising:
   a first tension member coupled to urge the first retractor blade to rotate in a first direction about the axis of rotation; and
   a second tension member coupled to urge the second retractor blade to rotate in a second direction, opposite the first direction, about the axis of rotation.

4. The apparatus of claim 1, wherein:
   the first slot extends into the third retractor blade;
   the first drive pin extends from the first retractor blade;
   the second slot extends into the third retractor blade; and
   the second drive pin extends from the second retractor blade.

5. The apparatus of claim 4, wherein:
   the first drive pin moves along a first rotation path about the axis of rotation when the first retractor blade rotates about the axis of rotation;
   the second drive pin moves along a second rotation path about the axis of rotation when the second retractor blade rotates about the axis of rotation; and
   a portion of the first drive pin engages with the first slot, an orientation of the first slot corresponds to the first rotation path such that a portion of a first torque is transferred from the first retractor blade to the third retractor blade throughout the first rotation path.

6. The apparatus of claim 5, wherein:
   the first coupling feature and the second coupling feature are configured such that when the first retractor blade is in a first angular orientation and the third retractor blade is in a third angular orientation, the second retractor blade is in a second angular orientation, the second angular orientation centered between the first angular orientation and the third angular orientation.

7. The apparatus of claim 1, wherein:
   an entirety of the first slot is straight and an entirety of the second slot is straight.

8. The apparatus of claim 1, wherein:
   the first slot includes a curved portion; and the second slot includes a curved portion.

9. The apparatus of claim 1, wherein:
   the first slot includes a straight portion; and
   the second slot includes a straight portion.

* * * * *